US012661329B2

(12) United States Patent
Reubinoff et al.

(10) Patent No.: US 12,661,329 B2
(45) Date of Patent: Jun. 23, 2026

(54) METHODS OF GENERATING OLIGODENDROCYTES

(71) Applicant: Hadasit Medical Research Services and Development Ltd., Jerusalem (IL)

(72) Inventors: Benjamin Eithan Reubinoff, Moshav Bar-Giora (IL); Etti Ben-Shushan, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 964 days.

(21) Appl. No.: 17/618,541

(22) PCT Filed: Jun. 11, 2020

(86) PCT No.: PCT/IL2020/050652
§ 371 (c)(1),
(2) Date: Dec. 13, 2021

(87) PCT Pub. No.: WO2020/250232
PCT Pub. Date: Dec. 17, 2020

(65) Prior Publication Data
US 2022/0233477 A1 Jul. 28, 2022

Related U.S. Application Data

(60) Provisional application No. 62/860,274, filed on Jun. 12, 2019.

(51) Int. Cl.
| | |
|---|---|
| *A61K 31/166* | (2006.01) |
| *A61P 9/10* | (2006.01) |
| *A61P 25/28* | (2006.01) |
| *A61P 37/06* | (2006.01) |
| *C12N 5/079* | (2010.01) |

(52) U.S. Cl.
CPC ............. *A61K 31/166* (2013.01); *A61P 9/10* (2018.01); *A61P 25/28* (2018.01); *A61P 37/06* (2018.01); *C12N 5/0622* (2013.01); *C12N 2500/02* (2013.01); *C12N 2501/105* (2013.01); *C12N 2501/115* (2013.01); *C12N 2501/33* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 9,833,439 | B2 | 12/2017 | Charbonnier et al. |
| 2017/0095512 | A1 | 4/2017 | Izrael et al. |

FOREIGN PATENT DOCUMENTS

WO    WO 2020/250232    12/2020

OTHER PUBLICATIONS

Thei, L. The Role of MAP Kinase Cascade in Neonatal Brain Response to Hypoxia Ischemic Insult. 2014, A thesis submitted for the degree of Doctor of Philosophy (Neuroscience) to University College London (Year: 2014).*
Suo, N. et al. Inhibition of MAPK/ERK pathway promotes oligodendrocytes generation and recovery of demyelinating diseases. Glia. Feb. 28, 2019;67(7):1320-1332 (Year: 2019).*
Casaccia, P. Anti-TANKyrase weapons promote myelination. Nature Neuroscience, 2011, 14, 945-947 (Year: 2011).*
Kondo, T. et al. A role for Noggin in the development of oligodendrocyte precursor cells. Developmental Biology, 2004, 267, 242-251 (Year: 2004).*
Watkins, T. et al. Distinct Stages of Myelination Regulated by γ-Secretase and Astrocytes in a Rapidly Myelinating CNS Coculture System. Neuron, 2008, 60, 555-569 (Year: 2008).*
Popescu, B. et al. Pathology of Multiple Sclerosis: Where Do We Stand? Continuum, 2013, 19(4 Multiple Sclerosis):901-921 (Year: 2013).*
Zhang, C. et al. The transcription factor NKX2-2 regulates oligodendrocyte differentiation through domain-specific interactions with transcriptional corepressors. J Biol Chem. Jan. 13, 2020;295(7):1879-1888 (Year: 2020).*
Jablonska, B. et al. Oligodendrocyte Regeneration after Neonatal Hypoxia Requires FoxO1-Mediated p27Kip1 Expression. J. Neurosci., 2012, 32(42):14775-14793 (Year: 2012).*
Lugowska, I. et al. Trametinib: a MEK inhibitor for management of metastatic melanoma. Onco Targets Ther. 2015, 8:2251-2259 (Year: 2015).*
Watkins, T. et al. Neuron, 2008, 60, 555-569 (Year: 2008).*
Jablonska, B. et al. J. Neurosci., 2012, 32(42):14775-14793 (Year: 2012).*
Kim, J. et al. Oct4-induced oligodendrocyte progenitor cells enhance functional recovery in spinal cord injury model. EMBO J. Oct. 23, 2015;34(23):2971-2983 (Year: 2015).*
Suo, N. et al. Glia. Feb. 28, 2019;67(7):1320-1332 (Year: 2019).*
Armstrong, R. et al. Journal of Neuroscience, 1992, 12 (4) 1538-1547 (Year: 1992).*
Requisition by the Examiner Dated Aug. 29, 2025 From the Innovation, Science and Economic Development Canada, Canadian Intellectual Property Office Re. Application No. 3,141,995. (4 Pages).
Notice of Reasons for Rejection Dated Dec. 17, 2024 From the Japan Patent Office Re. Application No. 2021-572926 and Its Translation Into English. (6 Pages).
International Preliminary Report on Patentability Dated Dec. 23, 2021 From the International Bureau of WIPO Re. Application No. PCT/IL2020/050652. (9 Pages).
International Search Report and the Written Opinion Dated Sep. 23, 2020 From the International Searching Authority Re. Application No. PCT/IL2020/050652. (16 Pages).
Baron et al. "PDGF and FGF-2 Signaling in Oligodendrocyte Progenitor Cells: Regulation of Proliferation and Differentiation by Multiple Intracellular Signaling Pathways", Molecular and Cellular Neuroscience, 15(3): 314-329, Mar. 2000.

(Continued)

*Primary Examiner* — Clinton A Brooks
*Assistant Examiner* — Nicola Maria Bauer

(57) ABSTRACT

A method of generating human mature oligodendrocytes is disclosed. The method comprises contacting a cell population which comprises human pre-oligodendrocytes with an inhibitor of the MAPK/ERK pathway under conditions that allow the pre-oligodendrocytes to differentiate into mature oligodendrocytes. Use of the MAPK/ERK pathway inhibitor for treating diseases is also disclosed.

13 Claims, 18 Drawing Sheets

(56) References Cited

OTHER PUBLICATIONS

Fyffe-Maricich et al. "The ERK2 Mitogen-Activated Protein Kinase Regulates the Timing of Oligodendrocyte Differentiation", The Journal of Neuroscience, 31(3): 843-850, Jan. 19, 2011.

Guardiola-Diaz et al. "Erk1/2 MAPK and mTOR Signaling Sequentially Regulates Progression Through Distinct Stages of Oligodendrocyte Differentiation", Glia, 60(3): 476-486, Mar. 2012.

Ishii et al. "Role of ERK1/2 MAPK Signaling in the Maintenance of Myelin and Axonal Integrity in the Adult CNS", The Journal of Neuroscience, 34(48): 16031-16045, Nov. 26, 2014.

Izrael et al. "Human Oligodendrocytes Derived From Embryonic Stem Cells: Effect of Noggin on Phenotypic Differentiation In Vitro and on Myelination In Vivo", Molecular and Cellular Neuroscience, 34(3): 310-323, Available Online Dec. 28, 2006.

Li et al. "MEK Is a Key Regulator of Gliogenesis in the Developing Brain", Neuron, 75(6): 1035-1050, Sep. 20, 2012.

Nishri et al. "Continuous Immune-Modulatory Effects of Human Olig2+ Precursor Cells Attenuating a Chronic-Active Model of Multiple Sclerosis", Molecular Neurobiology, 57(2): 1021-1034, Published Online Oct. 28, 2019.

Qu et al. "bFGF Protects Pre-oligodendrocytes from Oxygen/Glucose Deprivation Injury to Ameliorate Demyelination", Cell Mol Neurobiol 35: 913-920, Apr. 2, 2015.

Suo et al. "Inhibition of MAPK/ERK Pathway Promotes Oligodendrocytes Generation and Recovery of Demyelinating Diseases", Glia, 67(7): 1320-1332, Published Online Feb. 28, 2019.

Thei et al. "Extracellular Signal-Regulated Kinase 2 Has Duality in Function Between Neuronal and Astocyte Expression Following Neonatal Hypoxic-Ischaemic Cerebral Injury", The Journal of Physiology, 596(23): 6043-6062, Published Online Jul. 11, 2018.

Van Tilborg et al. "Impaired Oligodendrocyte Maturation in Preterm Infants: Potential TherapeuticTargets", Progress in Neurobiology, 136: 28-49, Jan. 2016.

Wang et al. "Enhancing Oligodendrocyte Myelination Rescues Synaptic Loss and Improves Functional Recovery After Chronic Hypoxia", Neuron, 99(4): 689-701, Published Online Aug. 2, 2018.

Wang et al. "Myelin Degeneration and Diminished Myelin Renewal Contribute to Age-Related Deficits in Memory", Nature Neuroscience, 23(4): 481-486, Published Online Feb. 10, 2020.

Wang et al. "Oligogenesis in the "Oligovascular Unit" Involves PI3K/AKT/mTOR Signaling in Hypoxic-Ischemic Neonatal Mice", Brain Research Bulletin, 155: 81-91, Feb. 2020.

Younes-Rapozo et al. "A Role for the MAPK/ERK Pathway in Oligodendroglial Differentiation In Vitro: Stage Specific Effects on Cell Branching", International Journal of Developmental Neuroscience, 27(8): 757-768, Published Online Sep. 1, 2009.

Notice of Reason(s) for Rejection Dated Jun. 4, 2024 From the Japan Patent Office Re. Application No. 2021-572926 and Its Translation Into English. (11 Pages).

Du et al. "Effects of the Notch Signalling Pathway on Hyperoxia-Induced Immature Brain Damage in Newborn Mice", Neuroscience Letters, 653: 220-227, Jul. 13, 2017. Abstract.

Wang et al. "Lingo-1 shRNA and Notch Signaling Inhibitor DAPT Promote Differentiation of Neural Stem/Progenitor Cells Into Neurons", Brain Research, 1634: 34-44, Mar. 1, 2016. Abstract.

Examination Report Dated Jul. 29, 2025 From the Australian Government, IP Australia Re. Application No. 2020291694. (3 Pages).

Communication Pursuant to Article 94(3) EPC Dated Dec. 17, 2025 From the European Patent Office Re. Application No. 20735699.9. (8 Pages).

Dizon et al. "The Bone Morphogenetic Protein Antagonist Noggin Protects White Matter After Perinatal Hypoxia-Ischemia", Neurobiology of Disease, XP 28226518A, 423(3): 318-326, Jun. 2011.

Fancy et al. "Axin2 as Regulatory and Therapeutic Target in Newborn Brain Injury and Remyelination", Nature Neuroscience, XP055233229, 14(8): 1009-1016, Published Online Jun. 26, 2011.

* cited by examiner

Final clinical score

METHODS OF GENERATING OLIGODENDROCYTES

RELATED APPLICATIONS

This application is a National Phase of PCT Patent Application No. PCT/IL2020/050652 having International filing date of Jun. 11, 2020, which claims the benefit of priority under 35 USC § 119(e) of U.S. Provisional Patent Application No. 62/860,274 filed on Jun. 12, 2019. The contents of the above applications are all incorporated by reference as if fully set forth herein in their entirety.

FIELD AND BACKGROUND OF THE INVENTION

The present invention, in some embodiments thereof, relates to a method of generating mature oligodendrocytes and, for use of the cells for the treatment of white matter injury (WMI).

White matter injury (WMI), including Periventricular Leukomalacia (PVL) is characterized by the death of the white matter of the brain. It can affect fetuses or newborns, and premature babies are at the greatest risk of the disorder. WMI often leads to nervous system and developmental problems in growing babies, particularly during the first or second year of life and may result in cerebral palsy. Researchers have identified a period of selective vulnerability in the developing fetal human brain, between 23 and 34 weeks of gestation, particularly before 32 weeks gestation, in which periventricular white matter is particularly sensitive to insults and injury. WMI is caused by a lack of oxygen or blood flow to the periventricular area of the brain, which results in the death or loss of brain tissue. WMI is diagnosed by ultrasound or MRI.

White matter disease or injury seen in premature infants manifests as diffuse hypomyelination and reduced white matter volume in the cerebral cortex. These abnormalities appear to result from the selective death or disordered development of the preoligodendrocyte (pre-OL) during episodes of hypoxia-ischemia (H-I) (Silbereis et al, 2010). Diffuse WMI manifests an overabundance of Olig-2-positive OL progenitor cells (OPCs) or pre-OL and depletion of mature MBP-positive OLs. Given the sensitivity of the OL lineage to hypoxic stress, the episodic recurrence of hypoxia-ischemia in extremely low birth weight (ELBW) neonates is a leading contributor to alterations in the OL lineage progression and WMI. Additional contributors are infection and inflammation. White matter injury is also a prominent feature of hypoxic ischemic encephalopathy (HIE) in term infants affected by intrapartum hypoxia-ischemia, wherein the intervascular zone of the deep periventricular region (the so-called "watershed") is primarily affected. In this population, white matter injury has been well characterized by various magnetic resonance imaging modalities, with abnormal findings correlating with long-term neurodevelopmental disability. At a cellular level, the injury and death of OL precursor cells underlies the decreased expression of mature myelin proteins and the resulting abnormalities of the cerebral white matter. Even utilizing therapeutic hypothermia, a large percentage of affected infants manifest clinical signs of this neuropathology over the long. Similarly, there are no therapies on the horizon for neonates undergoing complex congenital heart surgery, a population known to be at high risk for hypoxic-ischemic white matter disease both pre- and post-operatively.

At present there are no therapies available to treat white matter disease or injury in infants, including neonates, particularly PVL, particularly in low birth weight or premature infants.

Izrael et al. [5] reported on the use of noggin to enhance oligodendroglial differentiation and maturation.

The inhibition of MEK-ERK signaling was previously studied in oligodendroglial differentiation and was shown to inhibit differentiation into this lineage. Li et al., showed that knockout of MEK1/2 blocked the differentiation of radial glia into glial progenitors in the developing cortex in the embryo and postnatal leading to neurodegeneration and near absence of cortical astrocytes and oligodendrocytes [6].

Guardiola-Diaz et al., suggested that the inhibition of ERK1/2 attenuated the progression of early rat telencephalon oligodendroglial progenitors to late progenitors and did not have an effect on terminal differentiation into mature MBP-expressing cells [7].

Baron et al., showed that inhibition of MAPK by various molecules inhibited the differentiation of oligodendrocyte progenitors to mature oligodendrocytes [8].

Fyffe-Maricich et al., observed that deletion of ERK2 resulted in fewer GalC-expressing mature oligodendrocytes in mouse cortical cultures, and a delay in the expression of MBP in the mouse corpus callosum at postnatal day 10 in vivo. ERK1 deletion did not affect oligodendrocyte differentiation [9]. Younes-Rapozo et al., reported that the inhibition of MAPK/ERK pathway in rat cells significantly increased the number of immature oligodendroglial cells and decreased the number of mature oligodendroglial cells. Inhibition of MAPK/ERK pathway inhibited process extension giving rise to non-classified cells [10].

Ishii et al., showed that inducible conditional ablation of ERK1/2 in oligodendrocytes of the adult mouse CNS resulted in down regulation of myelin gene expression, followed by late onset partial loss of oligodendrocytes and progressive axonal degeneration [11].

Fancy (Nature Neuroscience 14:1009-1016, 2011) reported on the use of XAV939 to promote differentiation of oligodendrocyte progenitors (OLPs) isolated from mouse cerebral cortex.

Suo et al., Glia. 2019; 1-13 shows the effect of blocking MEK-ERK signalling by PD0325901 to augment oligodendrocyte differentiation in the mouse. However, the effect of PD0325901 was at an earlier stage of differentiation of the oligodendroglial lineage.

SUMMARY OF THE INVENTION

According to an aspect of the present invention, there is provided a method of generating human mature oligodendrocytes comprising contacting a cell population which comprises human pre-oligodendrocytes with an inhibitor of the MAPK/ERK pathway under conditions that allow the pre-oligodendrocytes to differentiate into mature oligodendrocytes, wherein no more than 70% of the cells of the cell population are oligodendrocyte progenitor cells (OPCs).

According to an aspect of the present invention, there is provided a method of treating a disease or disorder associated with a block in maturation of pre-oligodendrocyte into mature oligodendrocytes in a subject in need thereof, comprising administering to the subject a therapeutically effective amount of an inhibitor of the MAPK/ERK pathway, thereby treating the disease or disorder associated with a block in maturation of pre-oligodendrocyte into mature oligodendrocytes, with the proviso that when the disease is Multiple Sclerosis, the inhibitor is provided at the active plaque stage.

According to an aspect of the present invention, there is provided a method of preventing hypoxic injury in a fetus or neonate, comprising administering to the fetus or neonate a therapeutically effective amount of an inhibitor of the MAPK/ERK pathway, thereby preventing the hypoxic injury.

According to an aspect of the present invention, there is provided a method of screening for an agent capable of modulating hypoxic injured pre-oligodendrocytes comprising:

(a) subjecting pre-oligodendrocytes to hypoxic conditions to generate hypoxia-effected pre-oligodendrocytes;

(b) culturing the hypoxia-effected pre-oligodendrocytes in the presence of the agent under conditions that promote maturation of the pre-oligodendrocytes to mature oligodendrocytes; and (d) analyzing the amount of the mature oligodendrocytes, wherein an increase in the number of mature oligodendrocytes is indicative that the agent is a positive modulator of pre-oligodendrocytes.

According to embodiments of the present invention, the number of human pre-oligodendrocytes in the cell population is greater than the number of oligodendrocyte progenitor cells in the cell population.

According to embodiments of the present invention, the cell population comprises in-vivo differentiated human pre-oligodendrocytes.

According to embodiments of the present invention, the pre-oligodendrocytes express O4 and express at least a 20% decrease in nkx2.2 as compared to oligodendrocyte progenitor cells, as measured by RT-PCR.

According to embodiments of the present invention, the pre-oligodendrocytes do not express nkx2.2, as measured by immunofluorescence.

According to embodiments of the present invention, the inhibitor of the MAPK/ERK pathway comprises a MEK1/2 inhibitor.

According to embodiments of the present invention, the MEK1/2 inhibitor is selected from the group consisting of PD0325901, trametinib, AZD8330, AZD6244, U0126, PD184352, ARRY-142886 and PD98059.

According to embodiments of the present invention, the MEK1/2 inhibitor is PD0325901 or trametinib.

According to embodiments of the present invention, the method further comprises contacting the population of pre-oligodendrocytes with a tankyrase inhibitor.

According to embodiments of the present invention, the tankyrase inhibitor is XAV939.

According to embodiments of the present invention, the contacting is effected concomitantly with the inhibitor of MAPK/ERK pathway.

According to embodiments of the present invention, the method further comprises contacting the population of pre-oligodendrocytes with a BMP antagonist and/or a γ-secretase inhibitor.

According to embodiments of the present invention, the BMP antagonist comprises noggin.

According to embodiments of the present invention, the γ-secretase inhibitor comprises (N—N-(3,5-difluorphen-acetyl)-L-alanyl]-S-phenylglycine t-butyl ester (DAPT).

According to embodiments of the present invention, the method is effected ex vivo.

According to embodiments of the present invention, the method is effected in vivo.

According to embodiments of the present invention, the contacting comprises culturing the pre-oligodendrocytes in a culture medium comprising the inhibitor of the MAPK/ERK pathway.

According to embodiments of the present invention, the inhibitor of the MAPK/ERK pathway comprises a MEK1/2 inhibitor.

According to embodiments of the present invention, a concentration of the MEK1/2 inhibitor in the medium is between 0.01-0.5 μM.

According to embodiments of the present invention, a concentration of the MEK1/2 inhibitor in the medium is between 0.05-0.5 μM.

According to embodiments of the present invention, the culture medium further comprises at least one agent selected from the group consisting of a tankyrase inhibitor, a γ-secretase inhibitor and a BMP antagonist.

According to embodiments of the present invention, the concentration of the BMP antagonist in the medium is between 10 ng/ml-1 μg/ml.

According to embodiments of the present invention, the concentration of the γ-secretase inhibitor in the medium is between 0.1 μM-10 μM.

According to embodiments of the present invention, the human pre-oligodendrocytes were exposed to hypoxic conditions for at least 6 hours prior to the contacting.

According to embodiments of the present invention, the subject is a fetus.

According to embodiments of the present invention, the subject is a neonate.

According to embodiments of the present invention, the neonate is a premature neonate.

According to embodiments of the present invention, the administering to the fetus is effected in utero.

According to embodiments of the present invention, the disease is a diffuse white matter injury.

According to embodiments of the present invention, the diffuse white matter injury is a hypoxic injury.

According to embodiments of the present invention, the diffuse white matter injury is a result of infection.

According to embodiments of the present invention, the diffuse white matter injury is a result of inflammation.

According to embodiments of the present invention, the diffuse white matter injury is PVL.

According to embodiments of the present invention, the hypoxic injury is a result of stroke.

According to embodiments of the present invention, the hypoxic injury is a result of a birth asphyxia.

According to embodiments of the present invention, the administering is effected no more than 2 months following the hypoxic injury.

According to embodiments of the present invention, the method further comprises administering to the subject at least one additional agent selected from the group consisting of a tankyrase inhibitor, a BMP antagonist and a γ-secretase inhibitor.

According to embodiments of the present invention, the administering to the fetus is effected in utero.

According to embodiments of the present invention, the administering is effected at birth.

According to embodiments of the present invention, the fetus is at least 23 weeks.

According to embodiments of the present invention, the inhibitor is capable of crossing the blood/brain barrier.

According to embodiments of the present invention, the inhibitor is a MEK1/2 inhibitor.

According to embodiments of the present invention, the MEK1/2 inhibitor is selected from the group consisting of PD0325901, trametinib, AZD8330, AZD6244, U0126, PD184352, ARRY-142886 and PD98059.

According to embodiments of the present invention, the MEK1/2 inhibitor is PD0325901 or trametinib.

According to embodiments of the present invention, the method further comprises administering to the fetus or neonate at least one additional agent selected from the group consisting of a tankyrase inhibitor, a BMP antagonist and a γ-secretase inhibitor.

According to embodiments of the present invention, the pre-oligodendrocytes are generated by culturing pluripotent stem cells under conditions that promote differentiation of the pluripotent stem cells into pre-oligodendrocytes.

According to embodiments of the present invention, the pluripotent stem cells comprise embryonic stem cells (ESCs).

According to embodiments of the present invention, the pre-oligodendrocytes are generated from somatic cells.

According to embodiments of the present invention, the pre-oligodendrocytes are generated from neural stem or precursor or progenitor cells.

According to embodiments of the present invention, the pre-oligodendrocytes are generated from the fetal or adult brain.

According to embodiments of the present invention, the pluripotent stem cells comprise induced pluripotent stem cells (iPSCs).

According to embodiments of the present invention, the mature oligodendrocytes express a reporter protein.

According to embodiments of the present invention, the reporter protein is under control of a promoter of myelin basic protein (MBP).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
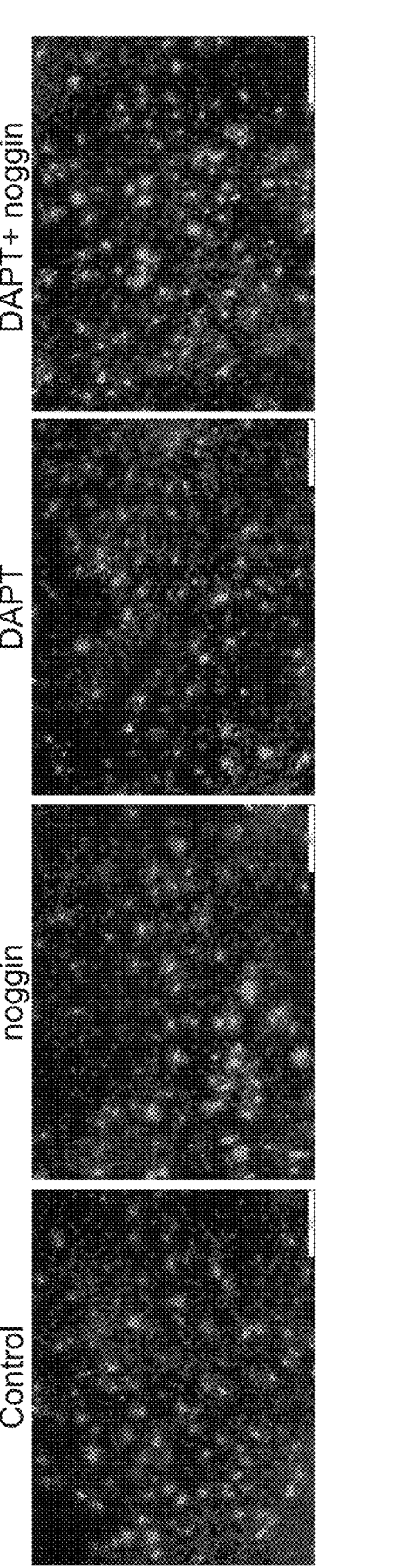
FIG. 1: Immuno-staining for MBP following 2 weeks treatment with vehicle, noggin, DAPT or DAPT+noggin indicates an increase in the proportion of MBP (green) mature oligodendrocytes in the presence of DAPT+noggin.

The present invention, in some embodiments thereof, relates to a method of generating mature oligodendrocytes and, for treatment of white matter injury.

According to an aspect of the present invention, there is provided a method of generating human mature oligodendrocytes comprising contacting a cell population which comprises human pre-oligodendrocytes with an inhibitor of the MAPK/ERK pathway under conditions that allow the pre-oligodendrocytes to differentiate into mature oligodendrocytes, wherein no more than 70% of the cells of the cell population are oligodendrocyte progenitor cells.

Mature oligodendrocytes may be distinguished from preoligodendrocytes both by structural and functional phenotypes.

Examples of a mature oligodendrocyte functional phenotype include, but are not limited to one or more, marker expression such as proteolipid protein (PLP), MBP expression, myelin-associated glycoprotein (MAG) and myelin oligodendrocyte glycoprotein (MOG).

Examples of mature oligodendrocyte structural phenotype include, but are not limited to, a branched and ramified phenotype and formation of myelin membranes.

Examples of a preoligodendrocyte functional phenotype include, but are not limited to migratory capacities as well as the potential to differentiate into a myelinating phenotype to effect myelination in vivo and in vitro.

Examples of pre-oligodendroctyre markers expression include, but are not limited to O4 sulfatide marker, with or without Olig2 and Sox10. An absence of terminal differentiation markers is also evident (e.g. MBP expression and myelin-associated glycoprotein (MAG)).

Examples of oligodendrocyte progenitor cell marker expression include, but are not limited to PDGF-receptor, Nkx2.2, Olig/2, NG2 (Chondroitin sulfate proteoglycan).

Typically, pre-oligodendrocytes express O4. Typically pre-oligodendrocytes express less nkx2.2 as compared to oligodendrocyte progenitor cells, as measured by RT-PCR (e.g. 20% less, 30% less, 40% less, 50% less).

In one embodiment, the pre-oligodendrocytes express O4 and do not express nkx2.2 (as measured by immunochemistry).

Examples of OPC structural phenotype include, but are not limited to elongated, bipolar or multipolar morphology. For example OPCs but not mature oligodendrocytes and astrocytes, incorporate bromodeoxyuridine (BrdU), a hallmark of mitosis.

The cell population which is differentiated into mature oligodendrocytes is one in which no more than 80% of the cell population are oligodendrocyte progenitor cells (OPCs). In one embodiment, no more than 70% of the cell population are OPCs. In one embodiment, no more than 60% of the cell population are OPCs. In one embodiment, no more than 50% of the cell population are OPCs. In one embodiment, no more than 40% of the cell population are OPCs. In another embodiment, no more than 30% of the cell population are OPCs. In still another embodiment, no more than 20% of the cell population are OPCs. In still another embodiment, no more than 10% of the cell population are OPCs.

According to a specific embodiment, the starting population may be one that comprises more pre-oligodendrocytes than OPCs.

The cell population typically comprises viable cells (at least 50% of the cells are viable, 60% of the cells are viable, 70% of the cells are viable, 80% of the cells are viable, 90% of the cells are viable or 95% of the cells are viable).

In one embodiment, the pre-oligodendrocytes in the cell population have been exposed to hypoxic conditions for more than 6 hours, more than 12 hours, more than 24 hours, between 24 hours-60 hours, between 12 hours-60 hours— for example about 48 hours.

Hypoxic conditions are typically below 5% oxygen, between 0.1-5%, 1-5%, e.g. about 1.3% oxygen.

Pluripotent stem cells include embryonic stem cells and induced pluripotent stem cells.

In one embodiment, the human preoligodendrocytes are generated from mesenchymal stem cells.

In one embodiment, the human preoligodendrocytes are generated from adult stem cells. Non-limiting examples of adult stem cells are neural stem cells and neural precursors.

In one embodiment, the human pre-oligodendrocytes are generated by reprogramming from somatic cells. [Nan Yang Wernig; Nature Biotechnology 2013; 31: 434-439; Fadi J Naj Tesar. Nature Biotechnology 2013; 31: 426-433].

Methods of generating human preoligodendrocytes from pluripotent stem cells include those disclosed in US Patent Application Nos: 20170095512, 20140322179 and 20060078543, the contents of which are incorporated herein by reference.

Other methods are described in the below references:

1. S. R. L. Stacpoole et al., "High Yields of Oligodendrocyte Lineage Cells from Human Embryonic Stem Cells at Physiological Oxygen Tensions for Evaluation of Translational Biology," *Stem Cell Reports, vol.* 1, no. 5, pp. 437-450, November 2013.

2. P. Douvaras et al., "Efficient Generation of Myelinating Oligodendrocytes from Primary Progressive Multiple Sclerosis Patients by Induced Pluripotent Stem Cells," *Stem Cell Reports*, vol. 3, no. 2, pp. 250-259, August 2014.

3. B.-Y. Hu, Z.-W. Du, and S.-C. Zhang, "Differentiation of human oligodendrocytes from pluripotent stem cells," *Nat. Protoc.*, vol. 4, no. 11, pp. 1614-1622, November 2009.

4. S. Wang et al., "Human iPSC-Derived Oligodendrocyte Progenitor Cells Can Myelinate and Rescue a Mouse Model of Congenital Hypomyelination," *Cell Stem Cell*, vol. 12, no. 2, pp. 252-264, February 2013.

The inhibitor of a protein of the MAPK/ERK pathway may be any inhibitor that reduces the amount or activity of one or more proteins that belong to the MAPK/ERK pathway. The MAPK/ERK pathway is well-known to the skilled person and is one of the four parallel mitogen activated protein kinase (MAPK) signaling pathways identified: ERK1/ERK2, JNK, p38 and ERK5.

The pathways are involved in cellular events such as growth, differentiation and stress responses (J. Biol. Chem. (1993) 268, 14553-14556). These four pathways are linear kinase cascades in that MAPKKK phosphorylates and activates MAPKK, and MAPKK phosphorylates and activates MAPK. To date, seven MAPKK homologs (MEK1, MEK2, MKK3, MKK4/SEK, MEKS, MKK6, and MKK7) and four MAPK families (ERK1/2, JNK, p38, and ERK5) have been identified. Activation of these pathways regulates the activity of a number of substrates through phosphorylation. These substrates include: transcription factors such as TCF, c-myc, ATF2 and the AP-1 components, fos and Jun; cell surface components EGF-R; cytosolic components including PHAS-I, p90rsk, cPLA2 and c-Raf-1; and cytoskeleton components such as tau and MAP2. MAPK signaling cascades are involved in controlling cellular processes including proliferation, differentiation, apoptosis, and stress responses.

Of the known MAPK signaling pathways, the MAPK/ERK pathway (also referred to as RAF-MEK-ERK pathway or Ras-Raf-MEK-ERK pathway) mediates proliferative and anti-apoptotic signaling from growth factors and oncogenic factors such as Ras and Raf mutant phenotypes that promote tumor growth, progression, and metastasis.

Within the context of the current invention a protein of the MAPK/ERK pathway includes STAT, AKT, ERK, MEK, IkB and IKK proteins, as discussed below.

In a preferred embodiment, the protein of the MAPK/ERK pathway is selected from the group consisting of MEK1/2 and ERK, and a combination thereof.

In one embodiment, the inhibitor of a protein of the MAPK/ERK pathway is selected from the group consisting of a STAT inhibitor, an AKT inhibitor, an ERK inhibitor, an MEK inhibitor, an IkB inhibitor, an IKK inhibitor.

According to a particular embodiment, the inhibitor of a protein of the MAPK/ERK pathway is not a RAF inhibitor.

Examples of ERK inhibitors include, but are not limited to SCH772984, XMD8-92, FR 180204 and GDC-0994.

Examples of AKT inhibitors include, but are not limited to MK-2206, perifosine, GSK690693.

IkB/IKK inhibitors include, but are not limited to IKK-16, Bardoxolone methyl, TPCA-1 and IMD 0354.

STAT inhibitors include, but are not limited to SH-4-54, fludarabine, S31-201 and cryptotanshinone.

Thus in a preferred embodiment, the inhibitor of a protein of the MAPK/ERK pathway is selected from the group consisting of an ERK-inhibitor, and a MEK1/2-inhibitor, or combinations thereof.

According to a particular embodiment, the inhibitor is a MEK1/2 inhibitor.

Examples of MEK1/2 inhibitors include but are not limited to AZD8330, AZD6244, U0126, PD0325901, trametinib, PD184352, ARRY-142886 and PD98059.

Exemplary concentrations of MEK1/2 inhibitors are between 0.01-5 μM, more preferably between 0.1-5 μM, 0.1-1 μM, or 0.25-0.5 μM.

Examples of tankyrase inhibitors are disclosed in US Patent Application No. 20170065587, the contents of which are incorporated herein by reference.

Examples of BMP antagonists include LDN-193189 (4-(6-(4-(piperazin-1-yl)phenyl)pyrazolo[1,5-a]pyrimidin-3-yl)quinoline; Yu et al (2008) Nat Chem Biol 4 33-41)), GDF3, Noggin, and dorsomorphin (6-[4-[2-(1-Piperidinyl) ethoxy]phenyl]-3-(4-pyridinyl)-pyrazolo[1,5-a]pyrimidine; Yu et al (2008) Nat Chem Biol 4 33-41)). Preferably the BMP antagonist is noggin (e.g. 100 ng/ml).

An example of a γ-secretase inhibitor is (N—N-(3,5-difluorphenacetyl)-L-alanyl]-S-phenylglycine t-butyl ester (DAPT) (e.g. 1 μM).

According to another aspect of the present invention, there is provided a method of treating a disease or disorder associated with a block in maturation of pre-oligodendrocyte into mature oligodendrocytes in a subject in need thereof, comprising administering to the subject a therapeutically effective amount of a MEK1/2 inhibitor, thereby treating the disease or disorder associated with a block in maturation of pre-oligodendrocyte into mature oligodendrocytes.

The subject may be of any age, prenatal or postnatal. The subject may be an adult, a child or an infant. In one embodiment, the subject is a fetus. In another embodiment, the subject is premature. In another embodiment, the subject is a neonate. In still another embodiment, the subject is an elderly subject, for example over 60, over 70 or over 80.

In one embodiment, the disease is multiple sclerosis (e.g. during the active plaque stage).

In another embodiment, the disorder is age-related cognitive decline—see for example Weng et al., Nature Neuroscience, Vol 23, April 2020, pages 481-486. The disease may be dementia or Alzheimer's Disease.

In one embodiment, the disease is spinal cord injury.

In one embodiment, the disease is hypoxic ischemic encephalopathy (HIE)

In one embodiment, the disease is brain trauma.

A "neonate" refers to a newborn child or mammal, particularly a newborn human. The term neonate is typically used in reference to a newborn or infant during approximately the first month or 4 weeks after birth, and may include any period beginning at birth up to approximately a month after birth.

An "infant" refers to a very young mammal, particularly a human, or a baby. The term infant is typically used in reference to a very young mammal during approximately the first year of age, and may include the period beginning at birth to approximately 1 year in age. The term infant(s) thus includes neonate(s).

The term "postnatal" relates to or refers to the period after childbirth, particularly including an infant immediately after or right after birth.

The term "prenatal" relates to or refers to before birth or during or relating to pregnancy. Pregnancy in a human lasts typically 38 weeks after conception or 40 weeks after the woman's/mother's last period.

A "premature" human infant refers to an infant born less than 37 weeks gestational age or an infant born before the developing organs are mature enough to allow normal human postnatal survival.

A "full term" human infant refers to an infant born at gestational age between 37 and 42 weeks. A "postmature" human infant refers to an infant born after 42 weeks gestation.

Preferably, the inhibitor of the MAPK/ERK pathway (e.g. MEK1/2 inhibitor) is capable of passing the blood brain barrier.

In one embodiment, the inhibitor of the MAPK/ERK pathway (e.g. MEK1/2 inhibitor) is provided via the uterus to the fetus.

According to a particular embodiment, the inhibitor of the MAPK/ERK pathway (e.g. MEK1/2 inhibitor) is administered within 6 hours of the hypoxic injury, within 12 hours of the hypoxic injury, within 24 hours of the hypoxic injury or within 48 hours of the hypoxic injury.

Additional agents that may be administered include, but are not limited to a tankyrase inhibitor, a BMP antagonist and a γ-secretase inhibitor as further described herein above.

It will be appreciated that the inhibitor of the MAPK/ERK pathway (e.g. MEK1/2 inhibitor) may also be provided preventatively (for example before birth, when contractions begin). The inhibitor of the MAPK/ERK pathway (e.g. MEK1/2 inhibitor) may be provided from week 38, week 39, week 40, week 41 or week 42 of pregnancy.

In one embodiment, the inhibitor of the MAPK/ERK pathway (e.g MEK1/2 inhibitor) is used in the intervention relating to white matter disease or injury in a term or pre-term infant, in DWMI OR PVL, or in infants at high risk of DWMI or PVL, or infants who have suffered hypoxia or reduced oxygen during pregnancy and/or delivery, or demonstrate DWMI or PVL lesions on MRI or ultrasound.

DWMI including PVL is an important factor in neurological impairment of infants, particularly premature infants. Risk factors for white matter disease or injury, including particularly DWMI or PVL, include prematurity, low Apgar score, relatively long periods of ventilation and oxygen inhalation, a more persistent presence of apneic spells, prolonged or repetitive variable decelerations (irregular abrupt decreases in fetal heart rate) during labor, respiratory distress syndrome type I (Ibari S et al (1995) Nihon Sanka Fujinka Gakkai Zasshi 47(11):1243-7). Also, infants born to mothers who suffered from preterm premature rupture of membranes, bacterial vaginosis, antepartum hemorrhage, preeclampsia, viral infection such as CMV and rota virus and clinical chorioamnionitis are at greater risk for white matter disease or injury or DWMI (Hatzidaki E et al (2009) Acta Obstet Hynecol Scand 88(1):110-5). Very low birth weight premature infants (VLBWI) are at risk for white matter disease or injury or DWMI, particularly those with chorioamnionitis or funisitis or neonatal sepsis (Silveira R et al (2008) J Pediatria 84(3):211-216), as well as necrotizing enterocolitis.

Infants with any one or more of the above noted risk factors are suitable to benefit from and candidate subjects for the methods of the present invention. Thus, in an aspect of the invention, an infant, including a neonate, at risk of DWMI, including PVL including having one or more risk factor, particularly including one or more of prematurity, low Apgar score, relatively long periods of ventilation and oxygen inhalation, a more persistent presence of apneic spells, prolonged or repetitive variable decelerations (irregular abrupt decreases in fetal heart rate) during labor, respiratory distress syndrome type I, infants born to mothers who suffered from preterm premature rupture of membranes, bacterial vaginosis, preeclampsia, viral infection during pregnancy, such as CMV and Rota virus, antepartum hemorrhage or clinical chorioamnionitis, very low birth weight premature infants (VLBWI), particularly those with chorioamnionitis or funisitis or neonatal sepsis, or nectronizing enterocolitis (NEC) is a subject of the methods of the invention and a subject for administration of the compositions of the invention in accordance with the method(s). In accordance with the method, the inhibitor of the MAPK/ERK pathway (e.g. MEK1/2 inhibitor) may be administered at birth, as quickly as possible upon birth, within a minute of birth, within minutes of birth, within a day after birth, or one or more times as quickly as possible after birth, or seconds, hours or days after birth.

In the event of diagnosed DWMI (e.g. PVL), predicted DWMI (e.g. PVL) or risk of DWMI (e.g. PVL), including, but not limited to documented hypoxia or loss of oxygen for a sustained period, fast and effective treatment is important, particularly to minimize effects that become evident after a delay or will manifest later in the infant's life. Faster treatment may result in less permanent or long-term damage and reduced myelin damage that cannot be corrected, less neuromotor damage. Ultrasounds and MRIs are utilized to assess or diagnose the type or extent of DWMI, (e.g. PVL) in the infant.

Thus, in accordance with the method of the invention, a pregnant woman at risk of neonatal hypoxia or premature delivery, including a woman who has had a previous child with hypoxia or white matter injury or who is at risk of premature delivery, may be administered the inhibitor of the MAPK/ERK pathway (e.g. MEK1/2 inhibitor) prior to, during, or at the outset of labor. The route of administration may be selected to provide rapid and effective delivery of the inhibitor directly or indirectly to the fetus, including delivery to the fetus in utero. Alternatively an infant delivered by such a pregnant woman may be administered the inhibitor of the invention at the time of birth or immediately or shortly thereafter, including at birth, seconds after birth, within minutes of birth, in less than an hour after birth, etc and monitored thereafter for oxygenation, hypoxia, or effects of hypoxia.

The inhibitor of the MAPK/ERK pathway (e.g. MEK1/2 inhibitor) may be used in methods of treatment of the human or animal body, such as a method of treating white matter disease or injury, particularly DWMI, including PVL and of alleviating, blocking or reducing myelin damage, OL damage, and/or neuromotor deficits, including those associated with neonatal hypoxia, which comprises administering to the mammal, particularly an infant, including a neonate, particularly an infant that is not born full term or full gestational age, an effective amount of the inhibitor of the MAPK/ERK pathway (e.g. MEK1/2 inhibitor). In an aspect of the methods, the agents of the invention may be used in instances of established, suspected or possible white matter damage or injury, including DWMI (e.g. PVL), in an infant or pre-term baby, including as agents in methods for prevention, treatment or amelioration of nerve injury, damage or compromise and complications that can, may or do result from DWMI and/or infant white matter injury such as DWMI.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

HESCs Culture, OPC Production and Oligodendrocyte Maturation:

Human ESCs (HES1 passages 21 to 42 with a normal karyotype) were cultured as described [12]. hESC colonies were picked up by means of collagenase IV (1 mg/ml; GIBCO-BRL, Gaithersburg, MD) and placed into ultralow adherent culture dishes (Thermo Scientific Nunc HydroCell) to favor sphere aggregation. Spheres were cultured in NDM media consisting of Neural Differentiation Medium (Gibco) and N2B27 supplements with 20 ng/ml FGF-2. Spheres were first patterned with the dual-SMAD inhibitors LDN193189 (1 µM, Cayman Chemical, Ann Arbor, MI) and SB431542 (5 µM, SB; PeproTech Inc, Rocky Hill, NJ) until day 4 when SB431542 was withdrawn and the spheres were further cultured for additional 10 days in the presence LDN193189 and FGF-2. At day 14, the spheres were caudalized and ventralized using 0.1 µM all-trans retinoic acid and 0.5 µM purmorphamine, respectively (PeproTech Inc, Rocky Hill, NJ). At day 35, spheres were switched to modified SATO media, consisting of DMEM/F12, 10 ng/ml biotin, 60 ng/ml progesterone, 16 µg/ml putrescine, 20 µg/ml human insulin, 100 µg/ml apotransferrin, 5 ng/ml sodium selenite, 100 µg/ml bovine serum albumin (BSA), 60 µg/ml N-acetyl cysteine and 2 µg/ml forskolin. The medium was further supplemented with 20 ng/ml FGF-2, 0.5 µM Purmorphamine, 5 ng/ml NT3 and 200 nM ascorbic acid. Media was changed every 3 days for 6-7 weeks. For differentiation, spheres were dissected into small clusters mechanically and plated onto poly-D-lysine/laminin-coated plates and cultured in modified SATO media supplemented with 5 ng/ml NT3, 10 ng/ml IGF-1, 60 ng/ml T3, 100 ng/ml noggin and 200 nM ascorbic acid for 2-4 weeks.

To block Notch signaling, the γ-secretase inhibitor, DAPT (N—[N-(3,5-difluorphenacetyl)-L-alanyl]-S-phenylglycine t-butyl ester), PeproTech Inc, Rocky Hill, NJ) was added freshly every other day to the cells to a concentration of 1 µM. To block MEK/ERK signaling, PD0325901 (PeproTech Inc, Rocky Hill, NJ) was added freshly every other day to the cells to a concentration of 0.25-0.5 µM.

Immunocytochemistry: Cells were fixed in 4% paraformaldehyde for 20 min, washed with PBS, blocked in blocking solution (5% donkey serum, 0.2% Triton X-100 in PBS) for 1 hour, and incubated for 2 hours with primary antibodies mouse anti-Olig2 (Millipore Corporation diluted 1:150) and mouse anti-Nkx-2.2 (Developmental Studies Hybridoma Bank, diluted 1:100). After washing, cells were incubated with secondary antibody, donkey anti-mouse Alexa-488 (Life Technologies, Inc.), for 1 hour before being mounted in VECTASHIELD™ mounting medium. For O4 staining, cells were blocked in blocking solution (5% donkey serum in DMEM/F12) for 1 hour, and incubated with mouse-anti O4 antibody (R&D System, diluted 1:100) for 2 hours. After washing, cells were fixed in 4% paraformaldehyde for 20 min, and incubated with secondary antibody, donkey anti-mouse Alexa-488 or Alexa-555 (Life Technologies, Inc.), for 1 hour before being mounted in VECTASHIELD™ mounting medium. For MBP staining, after fixation cells were washed with PBS+0.01% saponin, blocked in blocking solution (5% goat serum, 0.01% saponin in DMEM/F12) for 1 hour, and incubated with rat anti-MBP antibody (R&D System 1:100) for 2 hours. After washing, cells were incubated with secondary antibody, goat anti-rat antibody (Jackson laboratories, 1:100) for 1 hour before being mounted in VECTASHIELD™ mounting medium.

RNA extraction and RT-PCR: Total RNA was extracted from hESC-derived pre-OLs, using TRIzol (Invitrogen). Complementary DNA was transcribed using the qSCRIPT cDNA synthesis kit (Quanta Biosciences). For quantitative real-time PCR, TaqMan Assays-on-Demand gene expression products, TaqMan Universal PCR Master Mix, and ABI Prism 7900HT Sequence Detection System (Applied Biosystems, Forster City, CA) were used. Large ribosomal protein P0 (RPLP0) was used as an internal reference for normalization.

Plasmid construction and gene targeting: Oligonucleotide encoding the MBP-targeting sgRNA was custom ordered (hy.labs), hybridized and ligated into the BbsI restriction site of pX330-U6-Chimeric-BB-CBh-hSpCas9 vector (Addgene #42230). Homology arms from the human mbp locus were amplified from genomic DNA isolated from HES1 cells by nested PCR (5' arm: Chr18:74692386-74693344, 3' arm: Chr18:74691209-74692367). The PCR products was digested and ligated into PNTKV-2A-Tomato donor plasmid. Correct construction of each expression cassette was verified by sequence analysis.

For gene editing, HES1 cells were transfected with 2 µg of donor plasmid and 0.5 µg of pX330-U6-Chimeric-BB-CBh-hSpCas9 expression vector using X-tremeGENE 9 DNA transfection reagent (Roche). At 24 hours after transfection 0.3 µg/ml of puromycin and 50 µg/ml of neomycin (Sigma) were added to the culture medium. After 2 weeks of selection, individual resistant colonies were harvested for genotyping and banked.

Results

Factors enhancing maturation of oligodendrocytes derived from pluripotent stem cells: hESC were differentiated into Olig2-expressing precursors by culturing them in suspension for 6 weeks to give rise to OPCs co-expressing Olig2 and Nkx-2.2. To induce further differentiation towards O4$^+$ pre-oligodendrocyte cells (pre-OL), the OPCs were plated on laminin and allowed to differentiate for ten days in the presence of 100 ng/ml of noggin.

Figure 2:
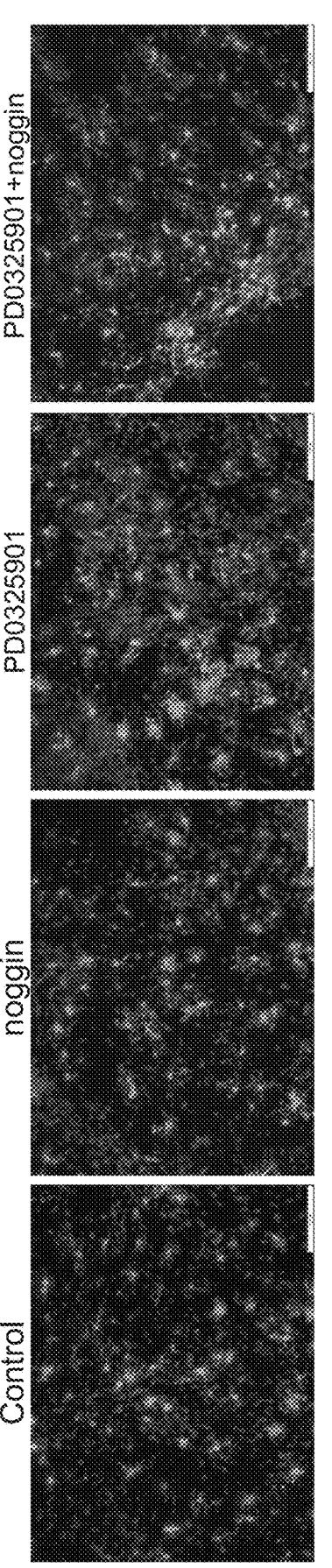
FIG. 2: Immuno-staining for MBP following 1 week treatment with vehicle, noggin, PD0325901 or PD0325901+ noggin indicates an increase in the proportion of MBP (green) mature oligodendrocytes in the presence of PD0325901.

Terminal maturation was obtained by further culture of pre-OL on laminin for 1-3 weeks. Maturation was enhanced after 2-3 weeks culture in the presence of noggin combined with DAPT (FIG. 1). A highly significant augmentation of maturation into MBP+ cells was observed in the presence of PD0325901. Maturation was obtained after a shorter culture period of 1 week. In addition, the MBP+ cells showed an enhanced branching of their processes (FIG. 2).

Figure 3:
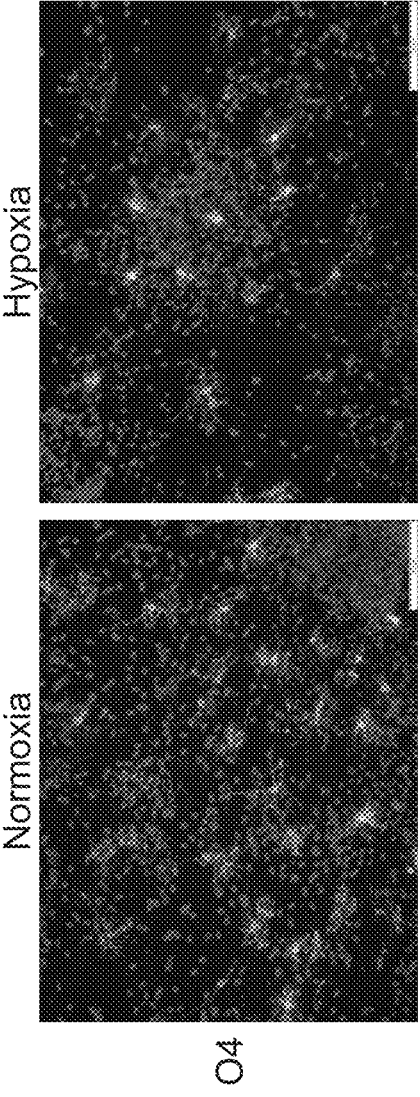
FIG. 3: Hypoxia for 48 hours results in a marked reduction in O4+-pre-OL (green) compared with cells incubated under normoxic environment.

Pluripotent stem cells for modeling hypoxic white matter injury in vitro: Differentiation into O4+ pre-oligodendrocyte cells (pre-OL) was induced as above. The cells were then exposed to 1.3% oxygen for 48 hours (hypoxia), and control cells were incubated at 21% oxygen (normoxia). Following hypoxic exposure, the expression of Olig2, Nkx-2.2 and O4 was tested by immunolabeling. It was found that exposure to hypoxia resulted in a marked decrease in the number of O4 expressing pre-OL compared with cells that were not exposed to hypoxia (FIG. 3).

Figure 4:
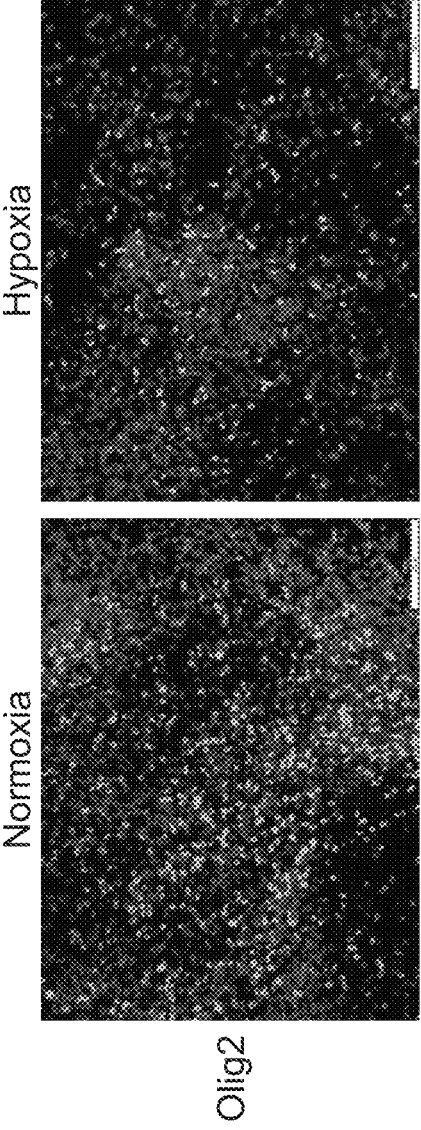
FIG. 4: Hypoxia for 48 hours decreased the number of Olig2 expressing cells (green) compared with cells incubated under normoxic conditions.
Figure 5:
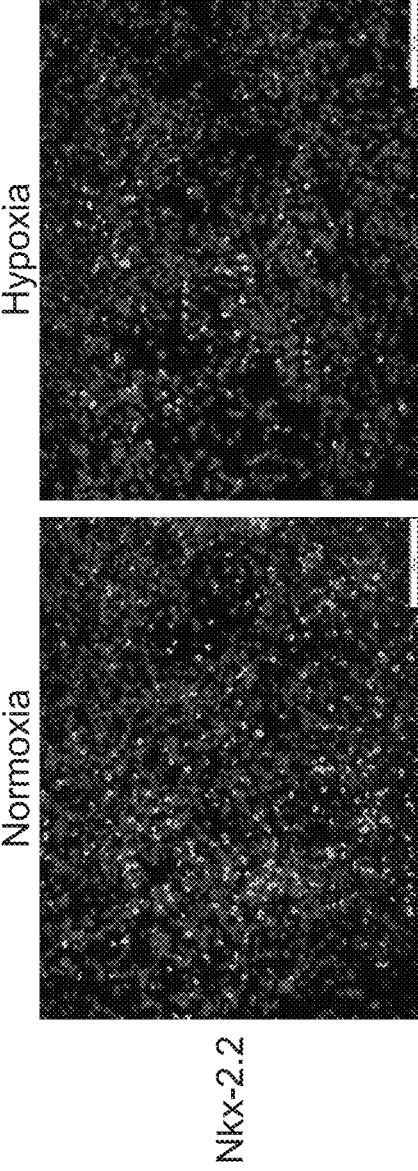
FIG. 5: Hypoxia for 48 hours results in a decrease in the number of Nkx-2.2 expressing cells (green) compared with cells incubated under normoxic conditions.
Figure 6:
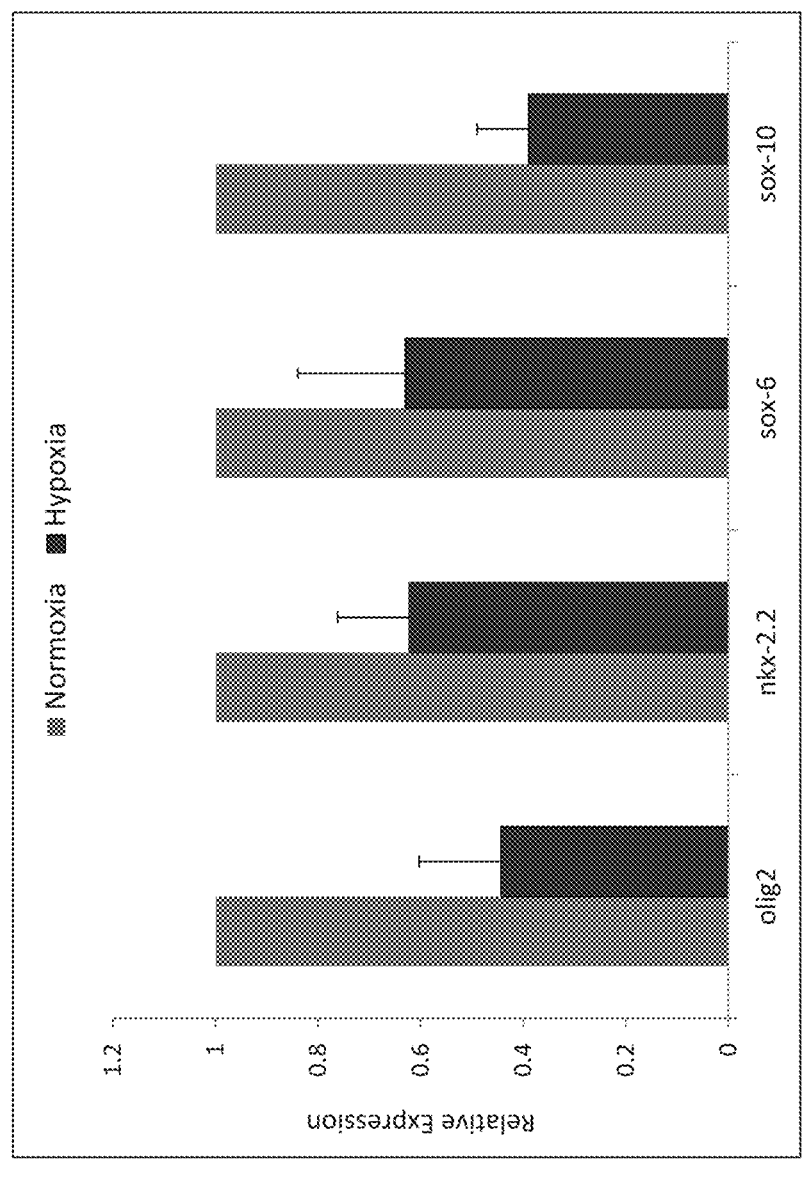
FIG. 6: Hypoxia for 48 hours results in a decrease in the expression of olig2, nkx-2.2, sox-6 and sox-10 genes compared with normoxic conditions.

Similarly, the hypoxic exposure led to a decrease in the number of cells expressing Olig2 (FIG. 4) or Nkx-2.2 (FIG. 5). Olig2+ cells were decreased by 50% following hypoxia. Concomitantly, down-regulation of transcripts of olig2, nkx-2.2, sox-6 and sox10 genes was observed, as tested by RT-PCR (FIG. 6). These data indicate that exposure to hypoxia leads to a loss of pre-OL, recapitulating the insult to pre-OL in diffuse WMI.

Figure 7:
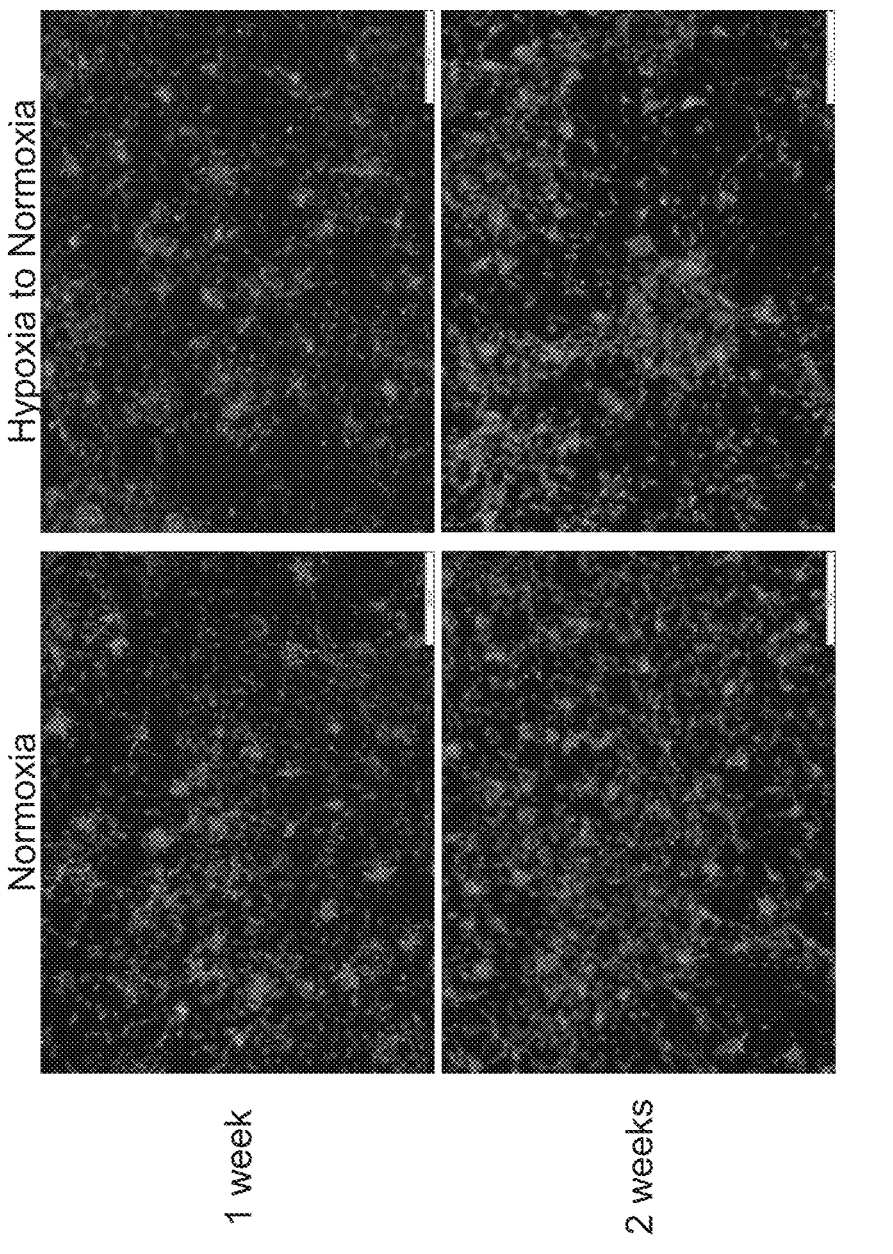
FIG. 7: Staining for O4 (red) 1 and 2 weeks following hypoxia indicates comparable percentages of O4+ pre-OL in normoxia and hypoxia-exposed cultures.

Studies in human tissues and in animal models of WMI showed that the hypoxia-induced pre-OL loss is followed by the generation of a new pool of pre-OL. However, the newly generated pre-OL fail to mature into myelin producing oligodendrocytes. Hence, the present inventors next tested whether pre-OL that survived the hypoxia period can further mature into myelin producing oligodendrocytes. For this purpose, the cells were transferred immediately following the hypoxia period into normoxia environment (21% O2) and were allowed to differentiate for further 1-2 weeks. Staining for O4, 1 and 2 weeks following the hypoxia revealed similar number of O4-expressing pre-OL in both the hypoxic and normoxic exposed cultures, indicating a full recovery of the pre-OL pool (FIG. 7). Thus, similar to the process of diffuse WMI in vivo; new pre-OLs were generated following hypoxia in vitro.

Figure 8:
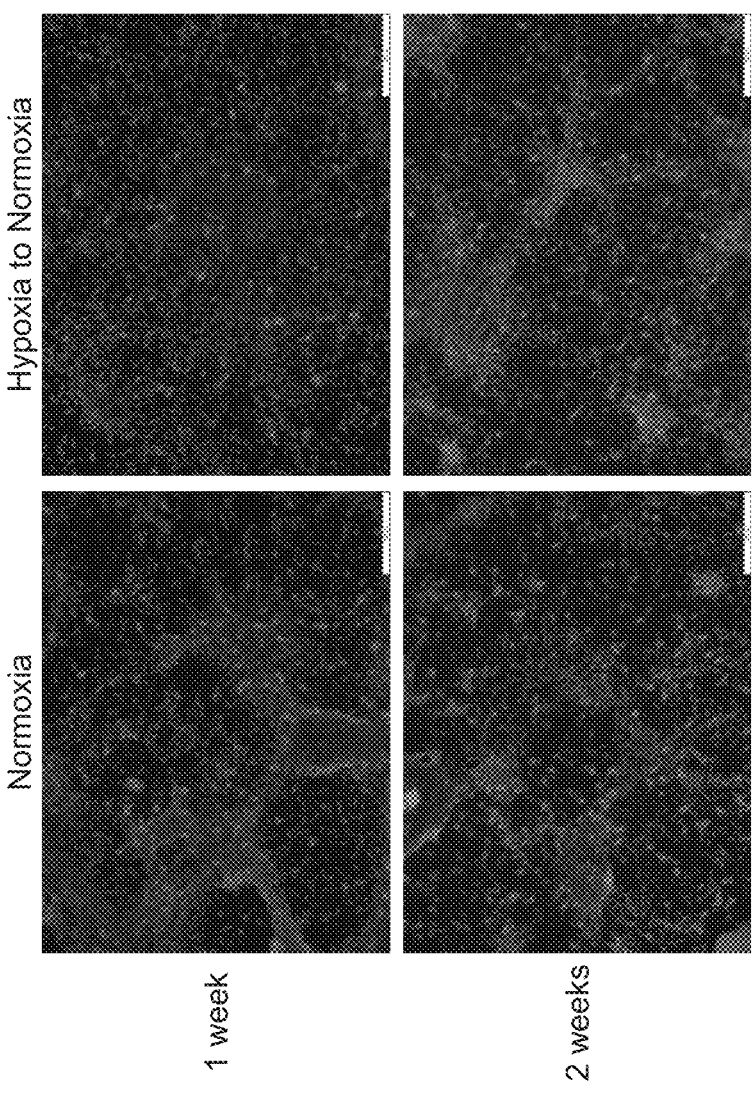
FIG. 8: Staining for MBP 1 and 2 weeks following 48 hr of hypoxia indicates a reduction in the percentage of mature oligodendrocytes in the cultures that were exposed to hypoxia compared with normoxia cultures.

To test whether these newly generated pre-OLs can further mature into myelin-producing oligodendrocytes, the production of myelin 1-2 weeks following the hypoxia period was analyzed. Immunostaining for myelin basic protein (MBP), a marker of mature oligodendrocytes revealed a lower proportion of mature MBP expressing cells in cultures that were exposed to hypoxia compared with normoxic conditions (FIG. 8). These data suggest that hypoxia results in a substantial maturation arrest of the pre-OL, similar to the differentiation and maturation failure of pre-OL in diffuse WMI. These findings suggest that the hESC-derived pre-OLs can serve as a reliable human model mimicking the process that occurs to fetal pre-OL following hypoxic injury.

Figure 9:
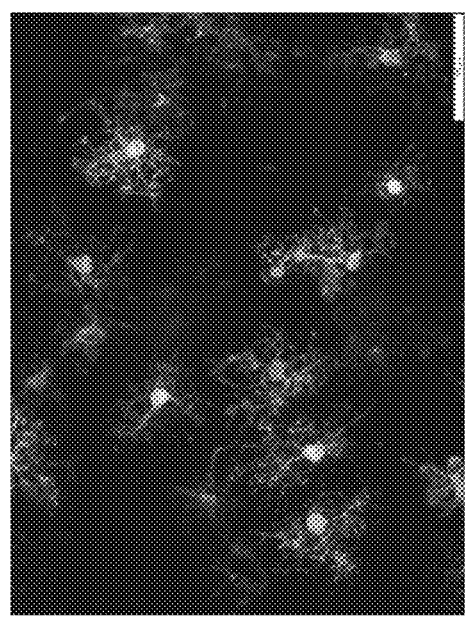
FIG. 9: A representative image of MBP-reporter mature oligodendrocytes co-expressing Tomato protein (red) and endogenous MBP protein (green).

To develop an efficient system that will allow screening for compounds that will promote the maturation of hypoxic arrested pre-OL into mature oligodendrocytes a reporter system for endogenous MBP was generated, using CRISPR/Cas9 gene targeting technology. The Cas9 nuclease and single-guided oligo designed to target the last exon of the human MBP gene was used to stimulate homology-directed repair with a donor construct encoding 2A-Tomato and neomycin expression cassette flanked by homology arms of the MBP locus. Notably, the human MBP gene has not previously undergone gene targeting in hESC. Differentiation of the MBP reporter cells into mature oligodendrocytes followed by staining to MBP protein revealed that Tomato expression faithfully reports on endogenous MBP expression (FIG. 9).

Figure 10:
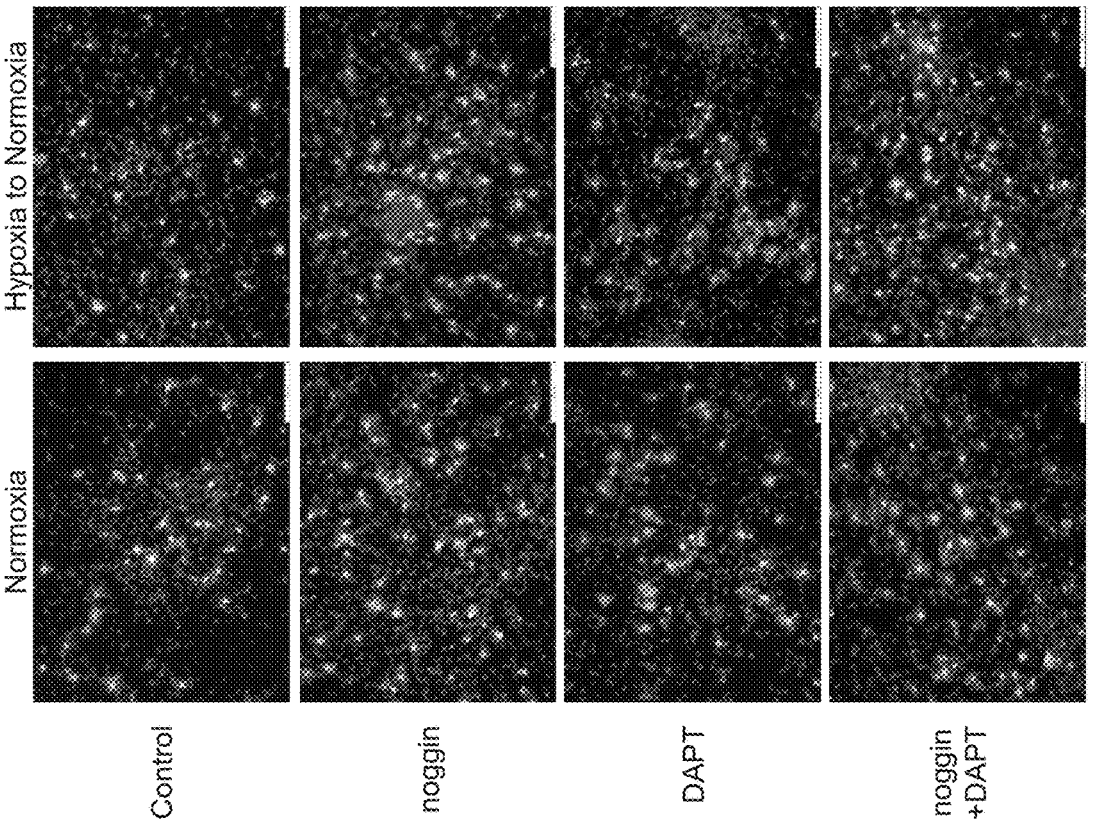
FIG. 10: Immuno-staining for MBP following 3 weeks treatment with noggin, DAPT or both. Under normoxia conditions (left panel) an increase in the proportion of MBP (green) and Tomato (red) co-expressing cells was observed in the presence of noggin as well as noggin+DAPTcompared with vehicle-treated control cells. In hypoxia-exposed cultures (right panel) noggin, DAPT and their combination increased the proportion of MBP (green) and Tomato (red) co-expressing cells compared with vehicle-treated control cells.

Oligodendrocyte development is a complex process that requires many different signals. To test whether the inhibition of pre-OLs differentiation following hypoxia is linked to BMP and Notch signaling pathways, pre-OLs were exposed to hypoxia for 48 hours and returned to normoxia conditions for 3 weeks in the presence of BMP antagonist noggin (100 ng/ml) or in the presence of 1 µM γ-secretase inhibitor DAPT which blocks the Notch signaling pathway (FIG. 10).

Compared with vehicle treated control cells, noggin resulted in a substantial increase in the proportion of MBP$^+$ Tomato$^+$ expressing mature oligodendrocytes both in cells under normoxia and after hypoxia exposure. These results indicated that blocking of BMP signaling promotes the differentiation of pre-OLs into mature oligodendrocytes. Moreover, blocking of BMP signaling following hypoxia overcomes the hypoxia-induced inhibition of differentiation.

In the presence of DAPT an increased differentiation into MBP$^+$ Tomato$^+$ mature oligodendrocytes was observed in hypoxia exposed cultures compared with vehicle treated control cultures. In contrast, blocking of Notch signaling in cells that were cultured under normoxia conditions, did not increase the proportion of MBP$^+$ Tomato$^+$ oligodendrocytes compared with vehicle treated control. These findings indicate that blocking Notch signaling following hypoxia can overcome the hypoxia-induced inhibition of differentiation.

Blocking of both BMP and Notch signaling pathways by co-treatment with noggin and DAPT resulted in a substantial increase in the percentage of MBP$^+$ Tomato$^+$ mature oligodendrocyte both in normoxia and hypoxia exposed cultures.

Taken together, these results indicate that combined blocking of both BMP and Notch signaling pathways promotes maturation of pre-OLs into MBP-expressing oligodendrocytes. In addition, we show that blocking either BMP or Notch signaling or the combined block of the two signaling pathways can overcome the maturation arrest of hypoxic-injured pre-OLs into MBP-expressing mature oligodendrocytes.

Figure 11:
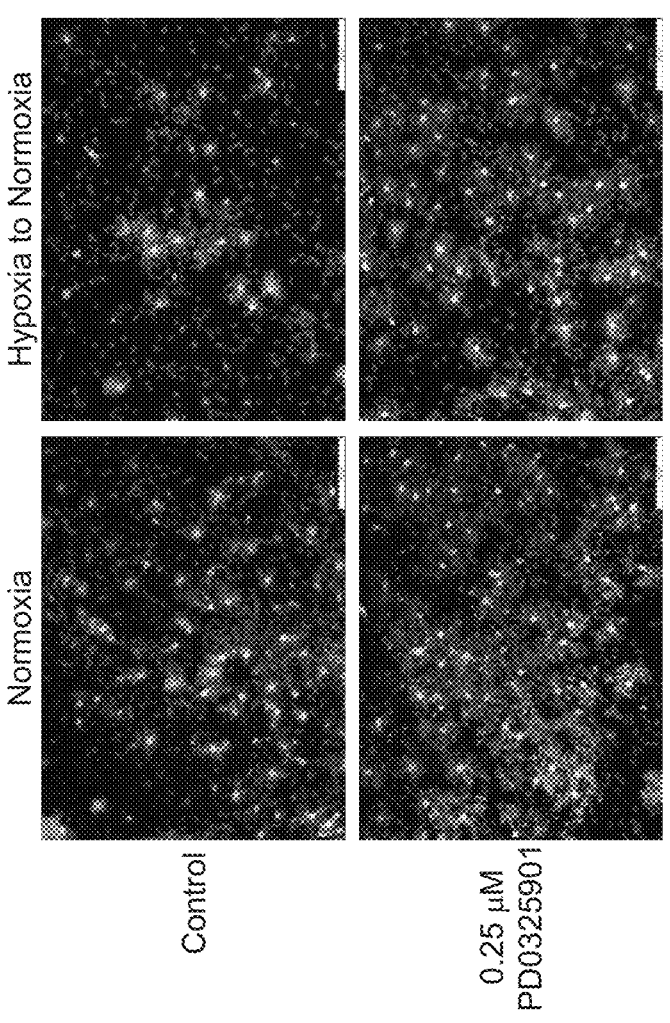
FIG. 11: Immuno-staining for MBP one week following hypoxia indicates increased number of MBP (green) Tomato (red) co-expressing oligodendrocytes in the presence of 0.25 µM PD0325901, both in normoxia and hypoxia-exposed cultures compared with vehicle treated (control) cultures.
Figure 12:
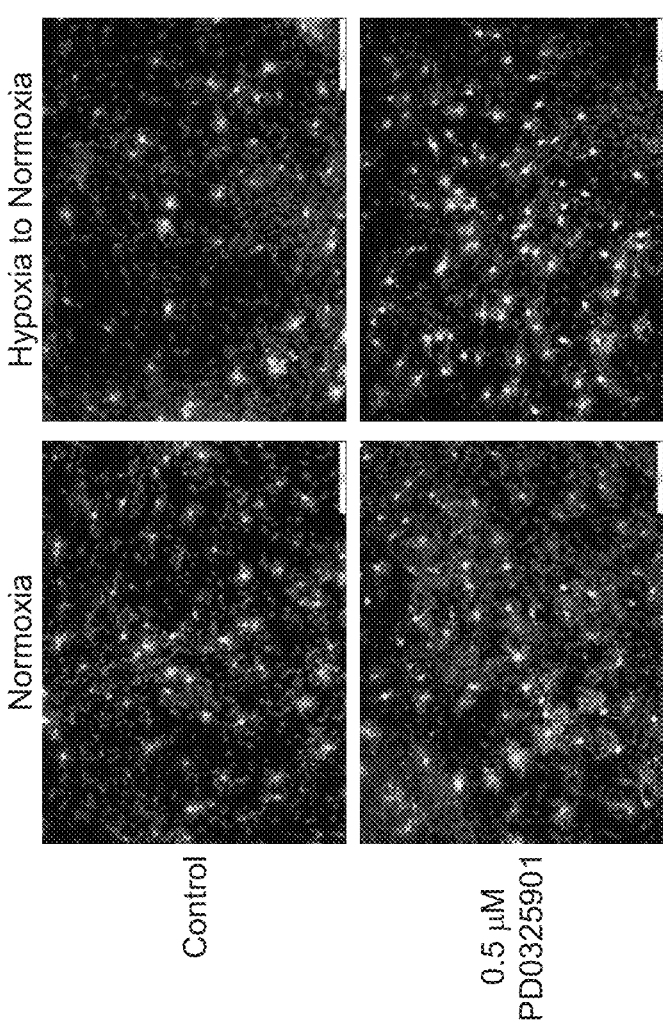
FIG. 12: Immuno-staining for MBP one week following hypoxia indicates increased number of MBP(green) Tomato (red) co-expressing oligodendrocytes in the presence of 0.5 µM PD0325901, both in normoxia and hypoxia-exposed cultures compared with vehicle treated (control) cultures.

In a search for additional signaling pathways that may have a role in the maturation arrest of hypoxic-injured pre-OLs, the effect of manipulating the MEK/ERK pathway was analyzed. The effect of PD0325901 which is a selective inhibitor of MEK/ERK signaling was analyzed. The cultures were treated with PD0325901 (0.25 µM or 0.5 µM) for one week following hypoxia (FIGS. 11 and 12). Remarkably, in the presence of PD0325901 a significant increase in the proportion of MBP$^+$ Tomato$^+$ oligodendrocytes was observed in normoxia compared with vehicle treated cultures, indicating that blocking MEK/ERK signaling promoted the maturation of pre-OLs.

In addition, branching of the processes of MBP+ oligodendrocytes was significantly enhanced in the presence of PD325901.

Moreover, in hypoxia-exposed cultures a marked increase in MBP$^+$ Tomato$^+$-expressing oligodendrocytes and in the branching of their processes was observed in the presence of PD0325901. It should be noted that the remarkable effect of PD0325901 on pre-OLs maturation was more prominent than treatment with noggin or DAPT and was observed already after one week of treatment compared to two-three weeks treatment that was required with noggin and/or DAPT.

Figure 13:
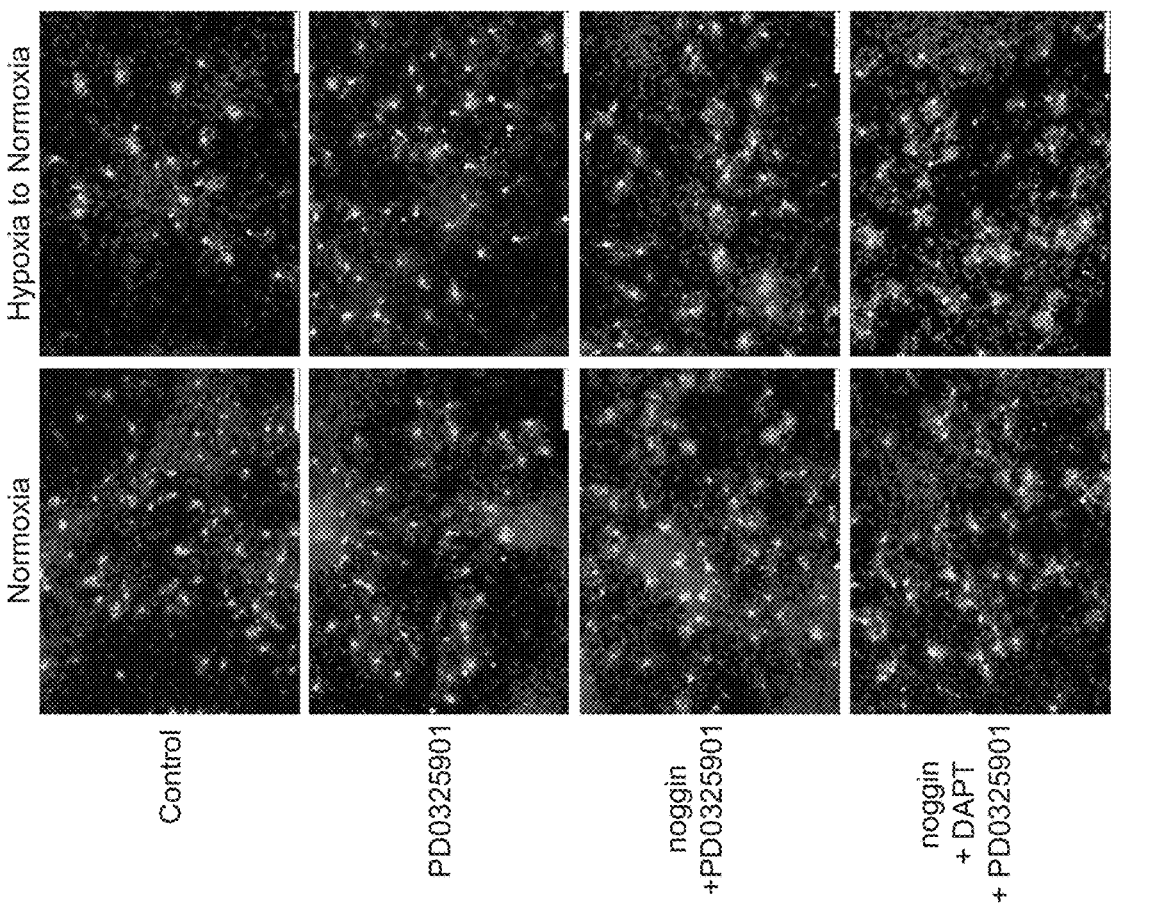
FIG. 13: Immuno-staining for MBP one week following hypoxia exposure showing increased proportion of MBP (green) Tomato (red) co-expressing oligodendrocytes in the presence of PD0325901 (0.25 µM), PD0325901+noggin, and PD0325901+noggin+DAPT, both in normoxia and hypoxia exposed cultures compared with vehicle treated cultures.

The effect on pre-OL maturation was also observed when the cultures were treated with 0.25 µM PD0325901 combined with noggin and DAPT, both under normoxia and following hypoxia (FIG. 13).

Figure 14:
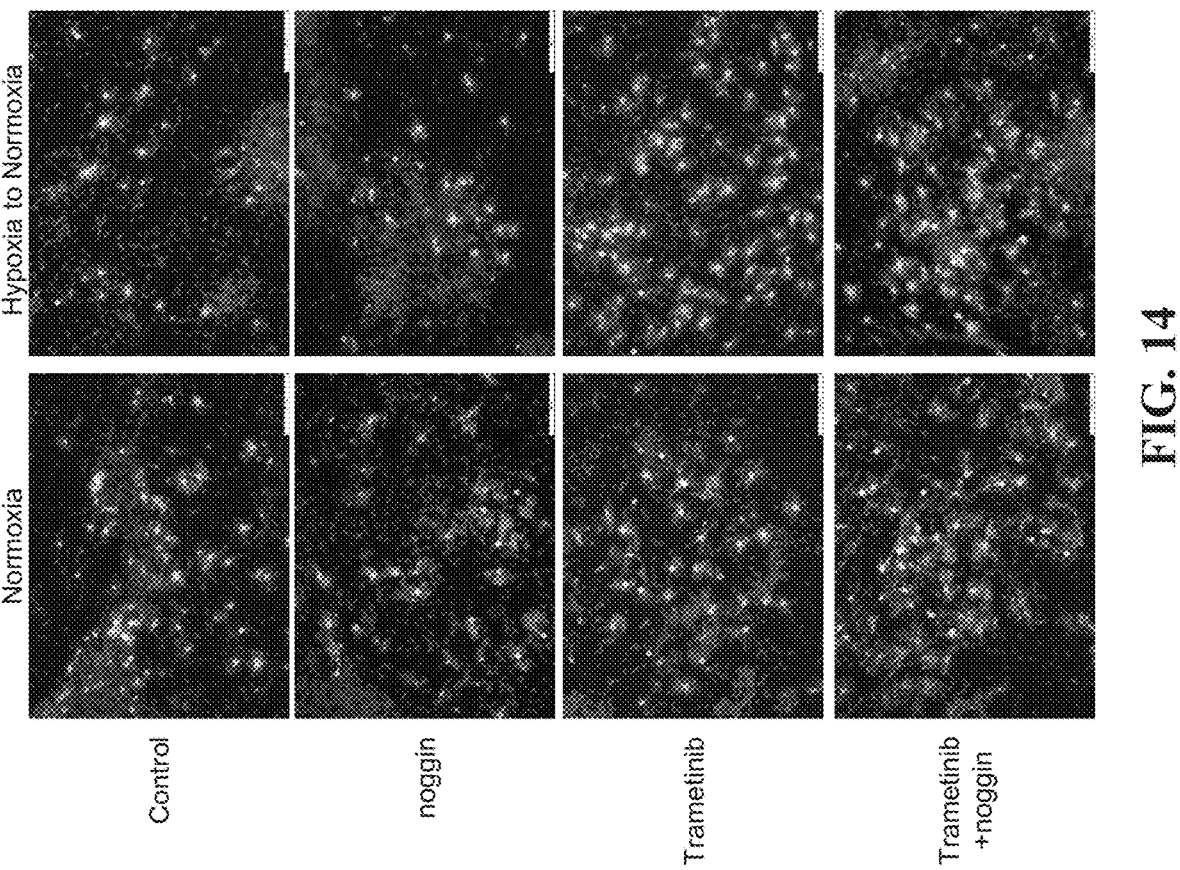
FIG. 14: Immuno-staining for MBP one week following hypoxia exposure showing increased proportion of MBP (green) Tomato (red) co-expressing oligodendrocytes in the presence of Trametinib (0.5 mM) and Trametinib+noggin, both in normoxia and hypoxia exposed cultures compared with vehicle treated cultures.

The effect on pre-OL maturation was also observed when the cultures were treated with 0.5 µM trametinib combined with noggin, both under normoxia and following hypoxia (FIG. 14).

These findings indicate that blocking of the MEK/ERK pathway promotes oligodendrocyte maturation under normoxia conditions and overcomes the hypoxia-induced arrest of pre-OLs maturation.

Moreover, the effect of MEK/ERK pathway inhibition is rapid and maturation occurs after one week.

REFERENCES FOR EXAMPLE 1

[1] S. R. L. Stacpoole et al., "High Yields of Oligodendrocyte Lineage Cells from Human Embryonic Stem Cells at Physiological Oxygen Tensions for Evaluation of Translational Biology," *Stem Cell Reports*, vol. 1, no. 5, pp. 437-450, November 2013.

[2] P. Douvaras et al., "Efficient Generation of Myelinating Oligodendrocytes from Primary Progressive Multiple Sclerosis Patients by Induced Pluripotent Stem Cells," *Stem Cell Reports*, vol. 3, no. 2, pp. 250-259, August 2014.

[3] B.-Y. Hu, Z.-W. Du, and S.-C. Zhang, "Differentiation of human oligodendrocytes from pluripotent stem cells," *Nat. Protoc.*, vol. 4, no. 11, pp. 1614-1622, November 2009.

[4] S. Wang et al., "Human iPSC-Derived Oligodendrocyte Progenitor Cells Can Myelinate and Rescue a Mouse Model of Congenital Hypomyelination," *Cell Stem Cell*, vol. 12, no. 2, pp. 252-264, February 2013.

[5] M. Izrael et al., "Human oligodendrocytes derived from embryonic stem cells: Effect of noggin on phenotypic differentiation in vitro and on myelination in vivo," *Mol. Cell. Neurosci.*, vol. 34, no. 3, pp. 310-323, March 2007.

[6] X. Li et al., "MEK Is a Key Regulator of Gliogenesis in the Developing Brain," *Neuron*, vol. 75, no. 6, pp. 1035-1050, September 2012.

[7] H. M. Guardiola-Diaz, A. Ishii, and R. Bansal, "Erk1/2 MAPK and mTOR signaling sequentially regulates progression through distinct stages of oligodendrocyte differentiation," *Glia*, vol. 60, no. 3, pp. 476-486, March 2012.

[8] W. Baron, B. Metz, R. Bansal, D. Hoekstra, and H. de Vries, "PDGF and FGF-2 Signaling in Oligodendrocyte Progenitor Cells: Regulation of Proliferation and Differentiation by Multiple Intracellular Signaling Pathways," *Mol. Cell. Neurosci.*, vol. 15, no. 3, pp. 314-329, March 2000.

[9] S. L. Fyffe-Maricich, J. C. Karlo, G. E. Landreth, and R. H. Miller, "The ERK2 Mitogen-Activated Protein Kinase Regulates the Timing of Oligodendrocyte Differentiation, " *J. Neurosci.*, vol. 31, no. 3, pp. 843-850, January 2011.

[10] V. Younes-Rapozo et al., "A role for the MAPK/ERK pathway in oligodendroglial differentiation in vitro: stage specific effects on cell branching," *Int. J. Dev. Neurosci.*, vol. 27, no. 8, pp. 757-768, December 2009.

[11] A. Ishii, M. Furusho, J. L. Dupree, and R. Bansal, "Role of ERK1/2 MAPK Signaling in the Maintenance of Myelin and Axonal Integrity in the Adult CNS," *J. Neurosci.*, vol. 34, no. 48, pp. 16031-16045, November 2014.

[12] M. Gropp and B. E. Reubinoff, "Lentiviral-RNA-Interference System Mediating Homogenous and Monitored Level of Gene Silencing in Human Embryonic Stem Cells," *Cloning Stem Cells*, vol. 9, no. 3, pp. 339-345, September 2007.

Example 2

Analysis of the Therapeutic Effect of MEK/ERK Inhibitors in an Animal Model of Hypoxia Induced WMI Pregnant C57/B mice will be monitored daily to determine the time of littering. At P3, dams and their pups will be randomly assigned (the pups' sexing not relevant in this study) to control or test groups and will be transferred in their cages for housing in a plexiglas oxygen-monitored chamber. The hypoxia-induced group will have 10% oxygen while the normoxia group will have normal oxygen conditions (~21%). The pups in the hypoxia-induced group will be daily treated with either PD0325901 (5 mg/kg) or Trametinib (5 mg/Kg) according to body weight, by oral gavage, from P3-P10 during hypoxia induction or from P11-P18 after hypoxia induction, or from P3-P18. From P11 all animals will have normal oxygen condition (~21%). At P10, P18 and P40, pups will be sacrificed for histology analysis. At P40, the pups will undergo rotarod and beam walking motor function tests.

Figure 15:
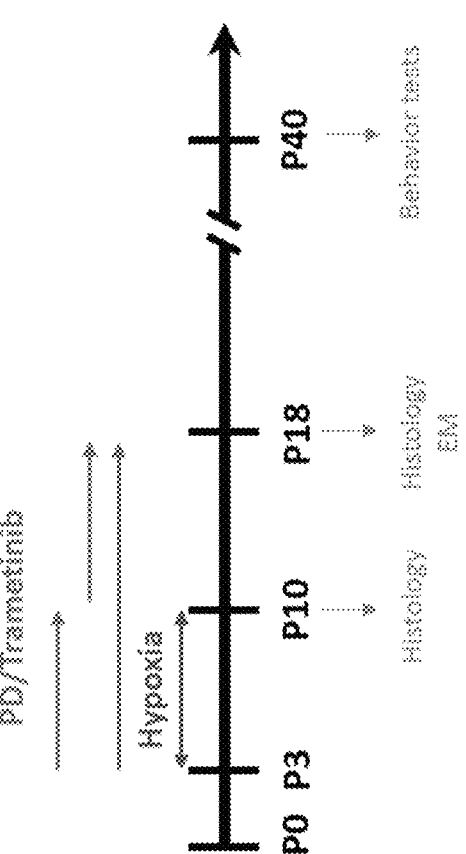
FIG. 15 is a graphical representation of the experimental design which can be used to assess the therapeutic effect of MEK/ERK inhibitors in an animal model of hypoxia induced WMI.

An outline of the experimental design is shown in FIG. 15.

Example 3

ICV Delivery of PD0325901 (PD) for Treatment of Chronic EAE

The Biozzi mouse model of Multiple Sclerosis: Biozzi ABH mice have genetic tendency to develop autoimmune diseases, and are used for many autoimmune models. The experimental autoimmune model in Biozzi mice is induced by immunization with spinal cord homogenate. Typically, mice develop an acute relapse, followed by remission, and after that a relapsing and progressive course of disease, resembling human multiple sclerosis (MS). Pathologically these mice exhibit typical features of human MS, including lesions of demyelination with variable degrees of axonal injury, in association with a neuroinflammatory process of T-cell and B-cell infiltration, microgliosis and astrogliosis. In the chronic phase of EAE there are typical immunopathological features resembling progressive MS, such as meningeal infiltrates and development of tertiary lymphoid-like tissue, partial closing of the blood-brain-barrier, and reduction in lesion activity with increase in astrogliosis. Therefore, this model is considered one of the most clinical-relevant experimental models of MS.

Materials and Methods

EAE was induced in Biozzi mice. Briefly, mice were inoculated subcutaneously at day 0 and day 7 in both hind flanks with 1 mg spinal cord homogenate emulsified in complete Freund's adjuvant supplemented with 3 μg M. Butyricum. Mice were monitored and scored daily in a blinded manner as follows: 0=normal, 1=limp tail, 2=impaired righting reflex, 3=hind-limb paresis; 4=complete hind-limb paralysis and 5=moribund/death. 10-14 days after the second relapse the mice were divided into two prospective experimental groups. The two groups exhibited comparable severity of disease course prior to cohorting. Mini-osmotic pumps were implanted intracerebroventricularly (ICV) at this time point to deliver PD (or vehicle) for 28 days in all mice. One group received PD (5 μg per day) and the other delivered vehicle only.

Figure 16:
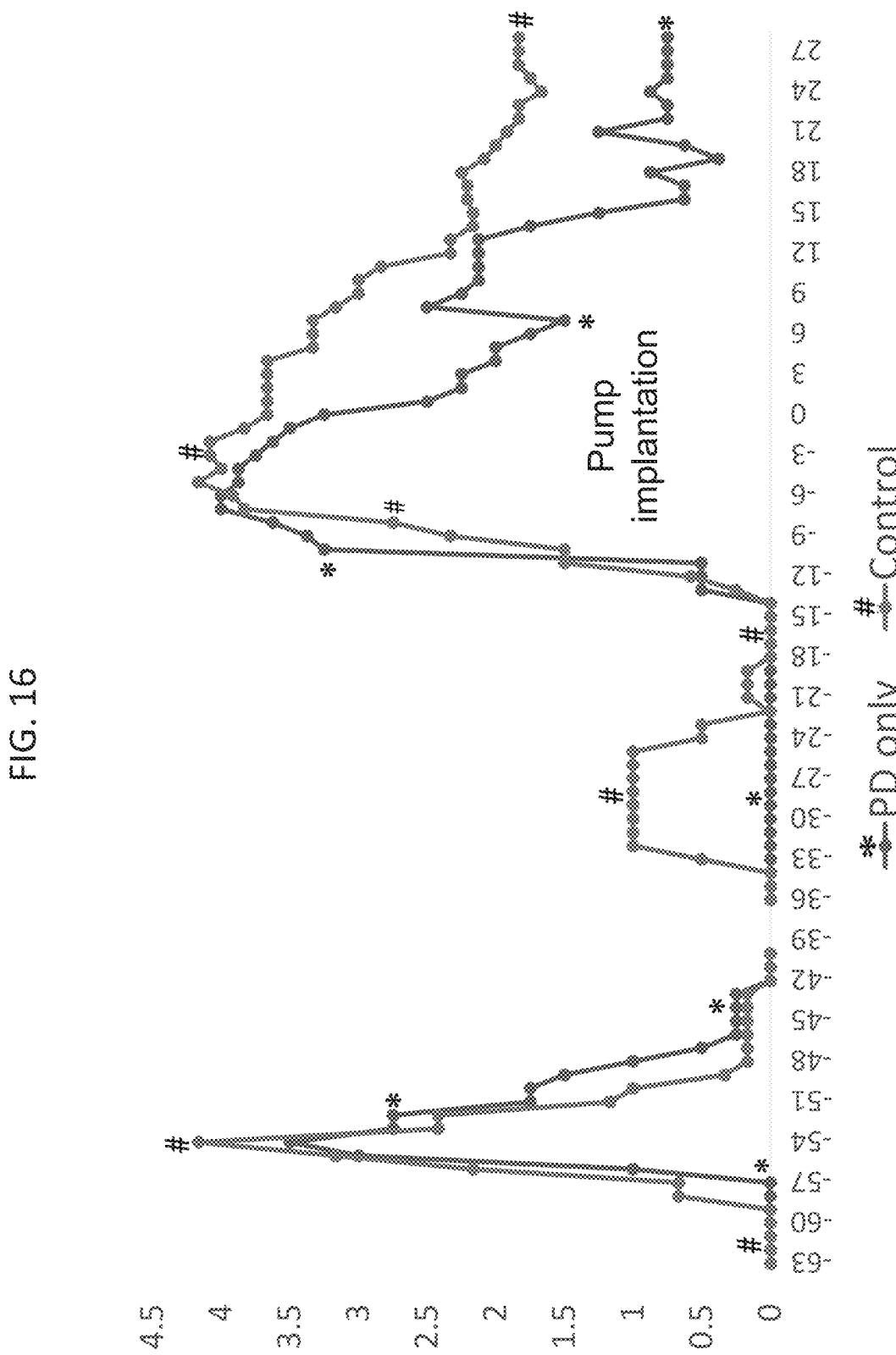
FIG. 16: Disease course in PD0325901-treated and vehicle-treated EAE mice, shown as average daily score per each group. Given the large variability in appearance of second relapse in this model, the pumps were implanted individually in mice at 10-14 days after the onset of second relapse. To enable comparison, the graphs were aligned according to the day of surgical implantation.
Figure 17A:
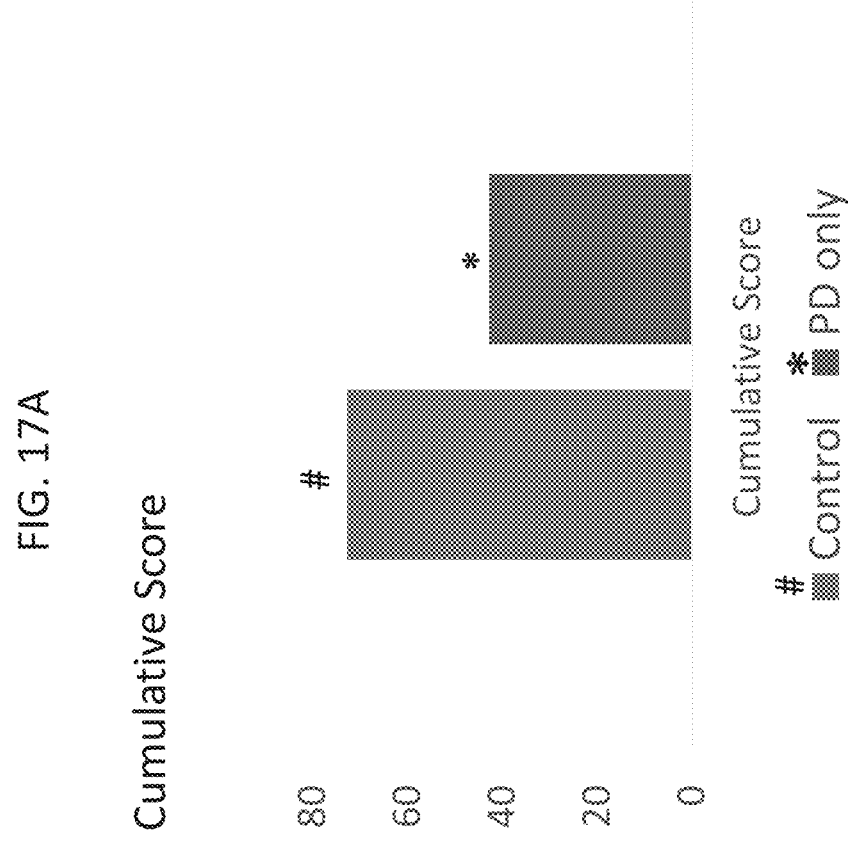
FIGS. 17A-B: Comparison of mean cumulative score (at days 0-28 from day of pump implantation) and of disease score at the last day of the experiment.
Figure 17B:
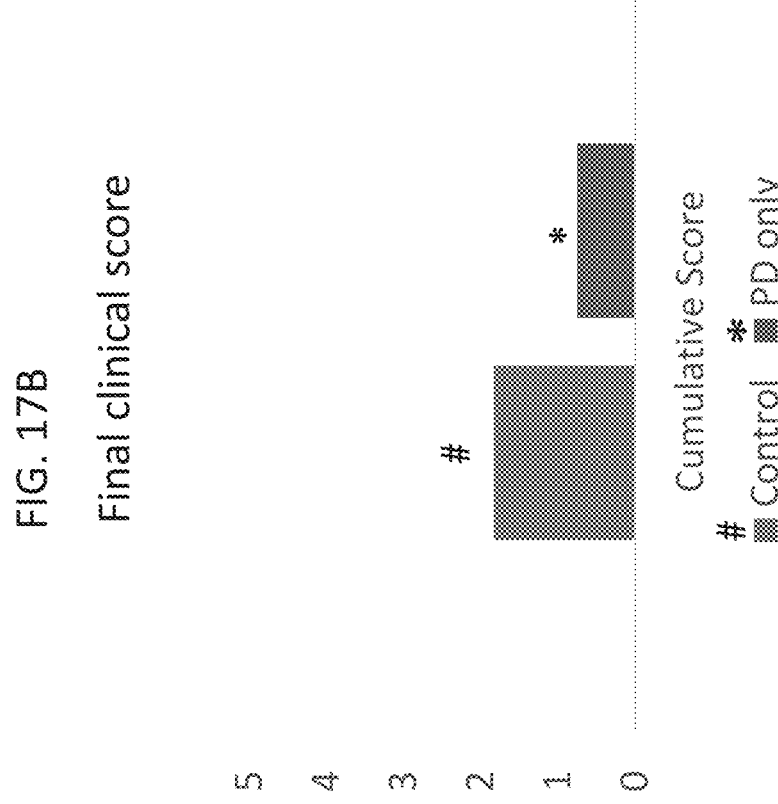

Results:

Two mice treated with PD developed a significantly milder disease course than the 3 vehicle-treated EAE mice, both in terms of mean cumulative score of disease (calculated from day of mini-osmotic pump implantation until experiment termination after 28 days), as well as according to the final clinical score at the day of termination of the experiment, when mice were sacrificed for pathological analysis (See FIGS. 16 and 17A-B).

CONCLUSION

Initial results suggest that ICV delivery of PD may attenuate EAE course at the chronic phase of disease.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method of generating human mature oligodendrocytes comprising:
   (a) culturing human pluripotent stem cells under conditions that produce a cell population comprising pre-oligodendrocytes which express O4, wherein no more than 70% of the cells of said cell population are oligodendrocyte progenitor cells (OPCs); and
   (b) contacting said cell population which comprises said pre-oligodendrocytes with an inhibitor of the MAPK/ERK pathway under conditions that allow the pre-oligodendrocytes to differentiate into mature oligodendrocytes.

2. The method of claim 1, the number of human pre-oligodendrocytes in the cell population is greater than the number of oligodendrocyte progenitor cells in the cell population.

3. The method of claim 1, wherein said pre-oligodendrocytes express at least a 20% decrease in nkx2.2 as compared to oligodendrocyte progenitor cells, as measured by RT-PCR.

4. The method of claim 1, wherein said pre-oligodendrocytes do not express nkx2.2, as measured by immunofluorescence.

5. The method of claim 1, wherein said inhibitor of the MAPK/ERK pathway comprises a MEK1/2 inhibitor.

6. The method of claim 5, wherein said MEK1/2 inhibitor is PD0325901 or trametinib.

7. The method of claim 1, further comprising contacting the population of pre-oligodendrocytes with a tankyrase inhibitor.

8. The method of claim 1, further comprising contacting the population of pre-oligodendrocytes with a BMP antagonist and/or a γ-secretase inhibitor.

9. The method of claim 8, wherein said BMP antagonist comprises noggin.

10. The method of claim 8, wherein said γ-secretase inhibitor comprises (N—N-(3,5-difluorphenacetyl)-L-alanyl]-S-phenylglycine t-butyl ester (DAPT).

11. The method claim 1, wherein said contacting comprises culturing said pre-oligodendrocytes in a culture medium comprising said inhibitor of said MAPK/ERK pathway.

12. The method of claim 11, wherein said culture medium further comprises at least one agent selected from the group consisting of a tankyrase inhibitor, a γ-secretase inhibitor and a BMP antagonist.

13. The method of claim 1, wherein said human pre-oligodendrocytes were exposed to hypoxic conditions for at least 6 hours prior to said contacting.

* * * * *